(12) United States Patent
Hooper

(10) Patent No.: US 9,182,398 B2
(45) Date of Patent: Nov. 10, 2015

(54) METHODS AND COMPOSITIONS FOR DETECTING FUNGI AND MYCOTOXINS

(75) Inventor: Dennis G. Hooper, Lewisville, TX (US)

(73) Assignee: Medical Service Consultation International, LLC, Carrollton, TX (US)

( * ) Notice: Subject to any disclaimer, the term of this patent is extended or adjusted under 35 U.S.C. 154(b) by 601 days.

(21) Appl. No.: 11/731,674

(22) Filed: Mar. 30, 2007

(65) Prior Publication Data

US 2008/0014582 A1    Jan. 17, 2008

Related U.S. Application Data

(60) Provisional application No. 60/787,754, filed on Apr. 1, 2006, provisional application No. 60/790,974, filed on Apr. 11, 2006.

(51) Int. Cl.
C12Q 1/68 (2006.01)
G01N 33/00 (2006.01)
G01N 33/53 (2006.01)
(Continued)

(52) U.S. Cl.
CPC ........ *G01N 33/56961* (2013.01); *C12Q 1/6895* (2013.01); *G01N 2469/10* (2013.01)

(58) Field of Classification Search
CPC ... C12Q 1/6895; G01N 33/53; G01N 33/535; G01N 33/564; G01N 33/569; G01N 33/577; G01N 2333/37; G01N 2333/44; G01N 2333/705; G01N 2469/00; G01N 2469/10; G01N 2469/20; G01N 2500/00; G01N 2800/00; G01N 2800/26; G01N 2800/40; G01N 2800/50; G01N 2800/52; G01N 2800/709
See application file for complete search history.

(56) References Cited

U.S. PATENT DOCUMENTS

| 4,683,202 A | 7/1987 | Muller et al. |
| 4,744,981 A | 5/1988 | Pavansasivam |
| 4,772,551 A | 9/1988 | Hart et al. |

(Continued)

FOREIGN PATENT DOCUMENTS

| EP | 1215282 | * | 6/2002 | ............ C12N 15/02 |
| WO | 96/21741 | | 7/1996 | |

(Continued)

OTHER PUBLICATIONS

Groopman et al., (P.N.A.S. 1984. vol. 81, pp. 7728-7731).*

(Continued)

*Primary Examiner* — Ja'Na Hines
(74) *Attorney, Agent, or Firm* — Barnes & Thornburg LLP

(57) ABSTRACT

The invention relates to a method of identifying a specific fungal species in patient tissue or body fluid. The method comprises the steps of extracting and recovering DNA of the fungal species from the patient tissue or body fluid, amplifying the DNA, hybridizing a probe to the DNA to specifically identify the fungal species, and specifically identifying the fungal species. The invention also relates to a method of identifying a mycotoxin in patient tissue or body fluid. The method comprises the steps of extracting and recovering the mycotoxin from the patient tissue or body fluid, contacting the mycotoxin with an antibody directed against the mycotoxin, and identifying the myocotoxin. Both of these methods can be used to determine if a patient is at risk for or has developed a disease state related to a fungal infection, and to develop an effective treatment regimen for the patient.

13 Claims, 4 Drawing Sheets

URINE TRICOTHECENES

(51) Int. Cl.
G01N 33/542 (2006.01)
G01N 33/569 (2006.01)

(56) References Cited

U.S. PATENT DOCUMENTS

| | | | |
|---|---|---|---|
| 4,800,159 A | 1/1989 | Muller et al. | |
| 4,906,452 A | 3/1990 | Sivam | |
| 5,261,394 A | 11/1993 | Mulligan et al. | |
| 5,426,027 A | 6/1995 | Lott et al. | |
| 5,776,694 A | 7/1998 | Sheiness et al. | |
| 6,210,345 B1 | 4/2001 | Van Brunt | |
| 6,268,222 B1 | 7/2001 | Chandler et al. | |
| 6,345,025 B1 | 2/2002 | Yamamiya | |
| 6,362,008 B1 | 3/2002 | Kohn et al. | |
| 6,372,430 B1 | 4/2002 | Morrison et al. | |
| 6,696,304 B1* | 2/2004 | Davies | 436/518 |
| 6,699,670 B2 | 3/2004 | Rothman et al. | |
| 6,846,631 B2 | 1/2005 | Beck et al. | |
| 6,872,523 B1 | 3/2005 | Iwen et al. | |
| 7,384,622 B2 | 6/2008 | Hata et al. | |
| 8,628,928 B2 | 1/2014 | Hooper | |
| 8,956,821 B2 | 2/2015 | Hooper | |
| 8,962,251 B2 | 2/2015 | Hooper | |
| 2001/0004813 A1 | 6/2001 | Hedman | |
| 2003/0054356 A1 | 3/2003 | Jacobson et al. | |
| 2003/0129600 A1 | 7/2003 | Morrison et al. | |
| 2003/0203412 A1* | 10/2003 | Vojdani | 435/7.3 |
| 2004/0023207 A1 | 2/2004 | Polansky | |
| 2004/0170981 A1 | 9/2004 | McKenney et al. | |
| 2005/0176023 A1 | 8/2005 | Ramon et al. | |
| 2008/0014582 A1 | 1/2008 | Hooper | |
| 2008/0108905 A1 | 5/2008 | Lurie | |
| 2010/0068718 A1 | 3/2010 | Hooper | |
| 2010/0075322 A1 | 3/2010 | Hooper | |
| 2010/0129821 A1 | 5/2010 | Fredricks | |
| 2011/0104684 A1 | 5/2011 | Hooper | |
| 2013/0059307 A1 | 3/2013 | Hooper | |
| 2013/0183697 A1 | 7/2013 | Hooper | |
| 2014/0221504 A1 | 8/2014 | Hooper | |
| 2014/0342927 A1 | 11/2014 | Hooper | |

FOREIGN PATENT DOCUMENTS

| | | |
|---|---|---|
| WO | WO98/50584 A2 | 11/1998 |
| WO | WO01/54653 A1 | 8/2001 |
| WO | WO2004/054359 A2 | 7/2004 |
| WO | 2007/023461 | 3/2007 |
| WO | WO 2008/051285 | 5/2008 |

OTHER PUBLICATIONS

Vetro (PhD. Thesis: Development of sensitive immunodiagnostics for determination of toxic residues (mycotoxins, drugs) in biological fluids and animal feeds. 2002).*
Brasel et al., (Archives of Environmental Health: An International Journal. Jun. 2004. vol. 59(6):317-323).*
Kierek-Jaszcuk et al., (Food and Agricultural Immunology. 1995. vol. 7(3):243-252).*
Fontelo et al., (Applied and Environmental Microbio. 1983. vol. 45(2): 640-643).*
Lee et al., (J. Assoc. Off. Anal. Chem. vol. 1989. 72. No. 2: 345-348).*
Koster et al., A Geographically Diverse Set of Isolates Indicates Two Phylogenetic Lineages Within Strachybotrys Chartarum, Can. J. Bot. 81: 633-643, 2003 (10 pages).
Niesters, et al., Rapid, Polymerase Chain Reaction-Based Identification Assays for *Candida* Species, Journal of Clinical Microbiology, Apr. 1993, p. 904-910 (7 pages).
Chen et al., Identification of Medically Important Yeasts Using PCR-Based Detection of DNA Sequence Polymorphisms in the Internal Transcribed Spacer 2 Region of the rRNA Genes, Journal of Clinical Microbiology, Jun. 2000, p. 2302-2310 (9 pages).
Henry et al., Identification of *Aspergillus* Species Using Internal Transcribed Spacer Regions 1 and 2, Journal of Clinical Microbiology, Apr. 2000, p. 1510-1515 (6 pages).
International Search Report and the Written Opinion of the International Searching Authority dated Oct. 17, 2008 filed in related International Application No. PCT/US07/0824921, filed Mar. 30, 2007 (21 pages).
Brasel et al, "Detection of airborne Stachybotrys chartarum macrocyclic trichothecene mycotoxins on particulates smaller than conidia," Applied and Environmental Microbiology, 2005; 71:114-122.
Lewis et al., "Detection of gliotoxin in experimental and human aspergillosis," *Infection and Immunity*; 2005; 73(1): 635-637.
Spiess et al., "Development of a LightCycler PCR assay for detection and qualification of Aspergillus fumigatus DNA in clinical samples from neutropenic patients," *Journal of Clinical Microbiology*, 2003; 41(5): 1811-1818.
Fox et al., "Detection of Aspergillus fumigatus mycotoxins: immunogen synthesis and immunoassay development," *Journal of Microbiological Methods*, 2004; 6+: 221-230.
Bialek et al., "PCR based identification and discrimination of agents of mucomycosis and aspergillosis in paraffin wax embedded tissue," *J. Clin. Pathol.*, 2005; 58:1180-1184.
Zorgani et al.,., "Detection pyrogenic toxin of *Staphylococcus aureus* in sudden infant death syndrome," *FEMS Immunology and Medical Microbiology*, 1999; 25: 103-108.
Stack et al., "Nonribosomal peptide synthesis in Apergillus fumigates and other fungi," *Microbiology*, 2007; 153(5): 1297-1306.
Ferns, "Evaluation of the role of real-time PCR in the diagnosis of invasive aspergillosis," *Leukemia & Lymphoma*, 2006; 41(1): 15-20.
Cruz-Perez et al., Detection and quantitation of Aspergillus fumigatus in pure culture using polymerase chain reaction, *Molecular and Cellular Probes*, 2001; 15:81-88.
GenBank AF138288 [online] Apr. 11, 2000 [retrieved on Feb. 23, 2012] retrieved from http://www.ncbi.nlm.nih.gov/nuccore/af138288.
De Vries et al. "Aspergillus vadensis, a new species of the group of black Aspergilli," Antoine Van Leeuwenhoek, 2005; 87(3): 195-203.
Ahern, *The Scientist*, 1995; 20(15):1-9.
Nielsen et al., "Yeast populations associated with Ghanaian cocoa fermentations analyzed using denaturing gradient gel electrophoresis (DGGE)," *Yeast*; 2005; 22:271-284.
Bennett et al., "Mycotoxins," *Clin. Microbiol. Rev.*, 2003; 16(3):497-516.
Zinkevich et al., FEMS Microbiology Ecology, 2000, 34: 147-155.
Andersson et al., Appl Environ Microbiol, 1997, 63(2): 387-393.
Quatrini et al., Hydrometallurgy, 2006, 83: 263-272.
Wulf-Durand et al., Appl. Environ. Microbiol., 1997, 63(7): 2944-2948.
Gregory et al., Toxicology Pathol., 2004, 32: 26-34.
Lee et al., J. Agric. Food Chem., 1990, 38: 444-448.
QuantiTox Kit from EviroLogix (Jul. 12, 2004).
Llobet-Brossa et al., Aquatic Microbial Ecol, 2002, 29: 211-226.
Yamanaka, Biochemistry and Environmental Biology: Chemolithoautotrophic Bacteria, 2008, pp. 7-9.
Bata et al., Appl Environ Microbiol, Mar. 1985, 49(3): 678-681.
McCormick et al., Toxins, 2011, 3: 802-814.
Willinger et al., Journal of Clinical Microbiology, 2003, 41(2): 581-585.
De Aguirre et al., Journal of Clinical Microbiology, 2004, 42(8): 3495-3504.
Hinrikson et al., Journal of Clinical Microbiology, 2005, 43(5): 2092-2103.
GenBank AF 138287 [online] Apr. 11, 2000 [retrieved Sep. 20, 2014] retrieved from http://www.ncbi.nlm.nih.gov/nuccore/af138287.
Brasel at el., Archives of Environmental Health: An international Journal, Jun. 2004, 59(6): 317-323.

(56) References Cited

OTHER PUBLICATIONS

U.S. Appl. No. 14/590,151, unpublished.
U.S. Appl. No. 14/590,173, unpublished.
Wei et al., Anal Biochem., Feb. 1987, 160(2): 399-408.
Brasilerio et al., "Genetic variability within *Fusarium solani* specie as revealed by PCR-fingerprinting based on pcr markers," Brazilian Journal of Microbiology, 2004, 35: 205-210.
Suga et al., "Phylogenetic analysis of the phytopathogenic fungus Fusarium solani cased on the rDNA-ITS region," Mycological Research, 2000, 104(10): 1175-1183.
Haugland et al., "Identification of putative sequence specific PCR primers for detection of the toxigenic fungal species *Stachybotrys chartarum*," Mol Cell Probes, Dec. 1998, 12(6): 387-96.
Mackay et al., "Real-time PCR in the microbiology laboratory," Clin. Microbiol. Infect, 2004, 10: 190-212.

\* cited by examiner

Nasal Secretion
TRICOTHECENES

| Tricothecenes Testing - Nasal Secretions | |
|---|---|
| Tricothecenes Value (ppb) | Number of Tests |
| 0 - 0.2 | 25 |
| 0.21 - 1.0 | 10 |
| 1.1 - 2.0 | 0 |
| 2.1 - 5.0 | 3 |
| 5.1 - 10 | 0 |
| 10.1 - 35 | 3 |
| > 35 | 1 |
| Total: | 42 |

SEQUENCE LISTING

<160> NUMBER OF SEQ ID NOS: 91

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
ttgcttcggc gggaacgccc cg                                        22

<210> SEQ ID NO 2
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 2
gcggagggat cattaccgag                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atcgatgcca gagccaagag                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
cggggagccc tctcgggggc                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgtaggtgaa cctgcggaag                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atcgatgccg gaaccaagag                                                   20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tgtctattgt acctgttgct tc                                                22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 8
cgtaggtgaa cctgcggaag					20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atcgatgccg gaaccaagag					20

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
ctctgtctga agattgtagt ctgagt				26

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgtaggtgaa cctgcggaag					20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atcgatgccg gaaccaagag					20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
cccgcctttg ctggccgcc					19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgtaggtgaa cctgcggaag                                        20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atcgatgccg gaaccaagag                                        20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggatctcttg gttctcgtat c                                      21

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cttgatctga ggttgaatag tg                                     22

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
aacgcacatt gcactttggg gtatc                                  25

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
cccgccattc atggccgccg gg                                     22

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 20
cgtaggtgaa cctgcggaag                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atcgatgccg gaaccaagag                                              20

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
aaagtatgca gtctgagttg attatc                                       26

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgtaggtgaa cctgcggaag                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atcgatgccg gaaccaagag                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25 cccaggggggc gagccgccgg                                             20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
```
cgtaggtgaa cctgcggaag                                          20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atcgatgccg gaaccaagag                                          20

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
acaccaacgt gaacactgtc tgaag                                    25

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgtaggtgaa cctgcggaag                                          20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
atcgatgccg gaaccaagag                                          20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
cgggcccgcc gtcatggccg                                          20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
cgtaggtgaa cctgcggaag                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atcgatgccg gaaccaagag                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
ccctcggggg cgagccgccg                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgtaggtgaa cctgcggaag                                              20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atcgatgccg gaaccaagag                                              20

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
ccacaccgaa cctcttgtta tagc                                         24

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cgtaggtgaa cctgcggaag                                              20
```

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
atcgatgccg gaaccaagag                                              20

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
cgggaataga cggccccgtg aaac                                         24

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcggagggat cattaccgag                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atcgatgcca gagccaagag                                              20

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
cccgccttta ctggccgccg g                                            21

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cgtaggtgaa cctgcggaag                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
atcgatgccg gaaccaagag                                              20

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic probe

<400> SEQUENCE: 46
tgttgcctcg gcgggccccg c                                            21

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
ggaaggatca ttaccgagtg                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
atcgatgccg gaaccaagag                                              20

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic probe

<400> SEQUENCE: 49
ttattgtacc ttgttgcttc ggcgg                                        25

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
cgtaggtgaa cctgcggaag                                              20

-continued

```
<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
atcgatgccg gaaccaagag                                                    20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
cgatctccgg gggacgggcc                                                    20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ctgtccgagc gtcattgctg                                                    20

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cgaggaccgg acgcggtg                                                      18

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 55
agacaccccc gaactctgcc tgaa                                                24

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cgtaggtgaa cctgcggaag                                                    20

<210> SEQ ID NO 57
```

```
<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
atcgatgccg gaaccaagag                                               20

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
cccgcctgcc aggccgccg                                                19

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cgtaggtgaa cctgcggaag                                               20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
atcgatgccg gaaccaagag                                               20

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61
cacccgtgtt tatttacctt attgc                                         25

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cgtaggtgaa cctgcggaag                                               20

<210> SEQ ID NO 63
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
atcgatgccg gaaccaagag                                                   20

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 64
cacccgtgtt tatcgtacct tgttg                                             25

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cgtaggtgaa cctgcggaag                                                   20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
atcgatgccg gaaccaagag                                                   20

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 67
ttgcttcggc gggagagccc cg                                                22

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gcggagggat cattaccgag                                                   20

<210> SEQ ID NO 69
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 69
atcgatgcca gagccaagag                                                    20

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
tgtctatctg taccctgttg cttcg                                              25

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cgtaggtgaa cctgcggaag                                                    20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
atcgatgccg gaaccaagag                                                    20

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
cctcggatca ggtagggata c                                                  21

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
atgcctgtcc gagcgtcatt                                                    20

<210> SEQ ID NO 75
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 75
ttcctccgct tattgatatg                                                 20

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76
acggatctct tggctctggc atc                                             23

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gcggagggat cattaccgag                                                 20

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ttcactgaat tctgcaattc ac                                              22

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
cctctgcccc ccgggcccgt g                                               21

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ggaaggatca ttaccgagtg                                                 20

<210> SEQ ID NO 81
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 81
ggagcccccc aggggcgag                                                    20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82
cggggaaccc cctcggggc                                                    20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
tgcgctcccc ccggggcag                                                    20

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
ggccccgtcc cccgatctcc g                                                 21

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
agtgaatcat cgagtctttg aac                                               23

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
acctgatccg aggtcaacct g                                                 21

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued

```
        probe

<400> SEQUENCE: 87
cgggcccgcc tgccaggccg                                                 20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88 ccgggggggtt tacacccccg                                                20

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
ccggggggca tctgcccccg g                                               21

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gcccccgaga gggctccccg                                                 20

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gtttcacggg gccgtctatt cccg                                            24
```

METHODS AND COMPOSITIONS FOR DETECTING FUNGI AND MYCOTOXINS

CROSS REFERENCE TO RELATED APPLICATIONS

This application claims priority under 35 U.S.C §119(e) to U.S. Provisional Application Ser. No. 60/787,754, filed on Apr. 1, 2006, and 60/790,974, filed on Apr. 11, 2006.

FIELD OF THE INVENTION

This invention relates to methods and compositions for detecting or identifying fungi or for detecting or identifying mycotoxins. More particularly, the invention relates to methods and compositions for detecting or identifying fungi and for detecting or identifying mycotoxins in the tissues or body fluid samples of patients.

BACKGROUND AND SUMMARY

Molds (i.e., toxigenic and other septate molds) are ubiquitous in the environment. Mold is the common name for various types of fungi. Molds are usually found in moist, warm environments. Because molds grow in wet or moist indoor environments, people are exposed to molds or their byproducts through either direct contact, or through the air, if molds or mold byproducts are aerosolized. Exposure to molds can cause a number of adverse effects including allergic reactions, asthma attacks, and infections, particularly in individuals with immune system deficiencies.

Adverse effects from molds may occur when individuals are exposed to large doses of chemicals, known as mycotoxins, which are fungal metabolites (Samson et al., 1985; Burge, 1990; Flannigan et al., 1991). Mycotoxins have toxic effects ranging from severe irritations, such as allergic reactions and asthma, to immuno-suppression and cancer. Most mycotoxins are cytotoxic and exert their effects by interfering with vital cellular processes such as protein, RNA, and DNA synthesis. As a result, mycotoxins may be damaging to the skin, the lungs, the gut, and the like. The combined outcome may increase the susceptibility of the exposed individual to infectious diseases and, possibly, to cancer. Almost all of the studies to date focus on disease induced by mycotoxins ingested in contaminated food (Baxter et al., 1981), but mycotoxins are secondary metabolites of fungal spores and can enter the body through the respiratory tract.

In heavily contaminated environments, neurotoxic symptoms related to airborne mycotoxin exposure have been reported (Croft et al., 1986). Skin is another potential route of exposure to the mycotoxins of several fungi which have caused cases of severe dermatosis (Vennewald and Wollina, 2005). These same molds may cause invasive mold infection among patients with diseases which render the patient immuno-suppressed such as leukemia, lymphoma, and many cancers (Kontoyiannis, D P et al, 2005). The mold infections in such patients are often fatal with a documented fatally rate of 92% (Paterson and Singh, 1999).

There are no current methods that have been developed for determining the presence of mycotoxins in patient tissues or body fluids. There are, however, methods available to the environmental areas and to the food industry to determine levels of mycotoxins, such as tricothecenes, Aflatoxins B1, B2, D1, and D2, and Ochratoxin A (e.g., Envirologix and VICAM kits) in environmental samples and foods.

A definitive and early diagnosis of a fungal infection is crucial for patient treatment and management. A diagnosis of a fungal infection is often rendered late in the disease process, often even as late as autopsy (Kontoyiannis et al, 2000; Vogeser et al., 1997). The reasons for the late diagnosis of fungal infections include the lack of good clinical specimens, the difficultly in differentiating invasive mold infections from other types of infections, the lack of identification of molds with special stains in pathological specimens (i.e., these assays have a high error rate, a low sensitivity, and low specificity), the lack of an ability to obtain an antibody-based diagnosis in immuno-compromised patients, and the lack of assays to determine the presence of mycotoxins or fungal DNA in the tissue or fluids of those patients.

Thus, a reliable, sensitive, specific, and rapid method for mold detection in patient body fluids and tissues is needed. Applicant's present invention is based on the idea that if mycotoxins can be identified in patient tissue or body fluids, the identification of mycotoxins may serve as a potential diagnostic method 1.) to identify patients at risk for developing disease states related to mold infections, or 2.) to rapidly determine the cause of diseases related to mold infections so that effective treatment regimens can be developed for patients exposed to molds and experiencing symptoms resulting from mold infection. Applicant's present invention is also based on the development of a reliable, sensitive, specific, and rapid method for detecting fungal DNA in patient body fluids and tissues.

The present invention provides methods for detecting and identifying, in patient tissue and body fluid specimens, 1.) mycotoxins produced by fungi, and 2.) fungal DNA from fungal spores. The present invention overcomes the deficiencies in the art by providing reliable, sensitive, and specific diagnostic tests for the presence of fungi and fungal toxins in patient tissue and body fluids. Applicant has developed mycotoxin and fungal DNA extraction procedures and has supplemented those methods by developing detection methods. The detection methods employ antibody-based identification for mycotoxins and, for fungal DNA, use amplification of DNA with primers that specifically and selectively amplify fungal DNA isolated from patient tissues and body fluids.

In one illustrative embodiment, a method is provided of identifying a specific fungal species in patient tissue or body fluid. The method comprises the steps of extracting and recovering DNA of the fungal species from the patient tissue or body fluid, amplifying the DNA, hybridizing a probe to the DNA to specifically identify the fungal species, and specifically identifying the fungal species.

In another embodiment, a method is provided of identifying a mycotoxin in patient tissue or body fluid. The method comprises the steps of extracting and recovering the mycotoxin from the patient tissue or body fluid, contacting the mycotoxin with an antibody directed against the mycotoxin, and identifying the myocotoxin. In another illustrative embodiment the method can further comprise the step of quantifying the mycotoxin. In illustrative embodiments, the body fluid can be selected from the group consisting of urine, nasal secretions, nasal washes, bronchial lavages, bronchial washes, spinal fluid, sputum, gastric secretions, seminal fluid, other reproductive tract secretions, lymph fluid, whole blood, serum, and plasma. In other illustrative embodiments, the mycotoxin can be selected from the group consisting of tricothecenes, Aflatoxin B1, Aflatoxin B2, Aflatoxin D1, Aflatoxin D2, and Ochratoxin A. In yet other illustrative embodiments, the tissue can be derived from a patient tissue biopsy and can be in a 10% formalin solution or in a paraffin block. In another embodiment, the antibody is bound to a bead dyed with a fluorochrome.

In yet another embodiment, a method is provided of determining if a patient is at risk for or has developed a disease state related to a fungal infection. The method comprises the steps of extracting and recovering a mycotoxin from a tissue or body fluid of the patient, contacting the mycotoxin with an antibody directed against the toxin, identifying the mycotoxin, and determining if the patient is at risk for or has developed the disease state related to the fungal infection.

In still another embodiment, a method is provided of determining if a patient is at risk for or has developed a disease state related to a fungal infection. The method comprises the steps of extracting and recovering DNA of a specific fungal species from a tissue or body fluid of the patient, amplifying the DNA, hybridizing a probe to the DNA to specifically identify the fungal species, and specifically identifying the fungal species.

In another embodiment, a kit is provided. The kit can comprise any one of the probes described herein and/or any one of the primer sets described herein. The kit can also comprise components for the extraction and recovery of DNA and components for DNA amplification and instructions for use of the kit.

In yet another embodiment, a kit is provided. The kit comprises components for the extraction and recovery of a mycotoxin from body fluid or tissue of a patient. In other embodiments, the kit can further comprise components for identification of the mycotoxin and instructions for use of the kit.

In still another embodiment, a kit is provided. The kit comprises a purified nucleic acid with a sequence selected from the group consisting of SEQ ID NO: 1 to SEQ ID NO: 89 or with a complement of a sequence selected from the group consisting of of SEQ ID NO: 1 to SEQ ID NO: 89.

In another illustrative embodiment, a purified nucleic acid is provided. The nucleic acid comprises a sequence of SEQ ID NO: 1 to SEQ ID NO: 89 or a complement of a sequence of SEQ ID NO: 1 to SEQ ID NO: 89. In another illustrative embodiment, a nucleic acid is provided that hybridizes under highly stringent conditions to a sequence comprising a sequence of SEQ ID NO: 1 to SEQ ID NO: 89 or that hybridizes under highly stringent conditions to a complement of a sequence of SEQ ID NO: 1 to SEQ ID NO: 89.

In yet another embodiment, a method of detecting an antibody to a mycotoxin in a patient tissue extract or body fluid is provided. The method comprises the steps of contacting the patient tissue extract or body fluid with a mycotoxin or a mycotoxin antigen coupled to a bead wherein the bead is dyed with a fluorochrome, and detecting the antibody.

DESCRIPTION OF THE ILLUSTRATIVE EMBODIMENTS

Figure 1:
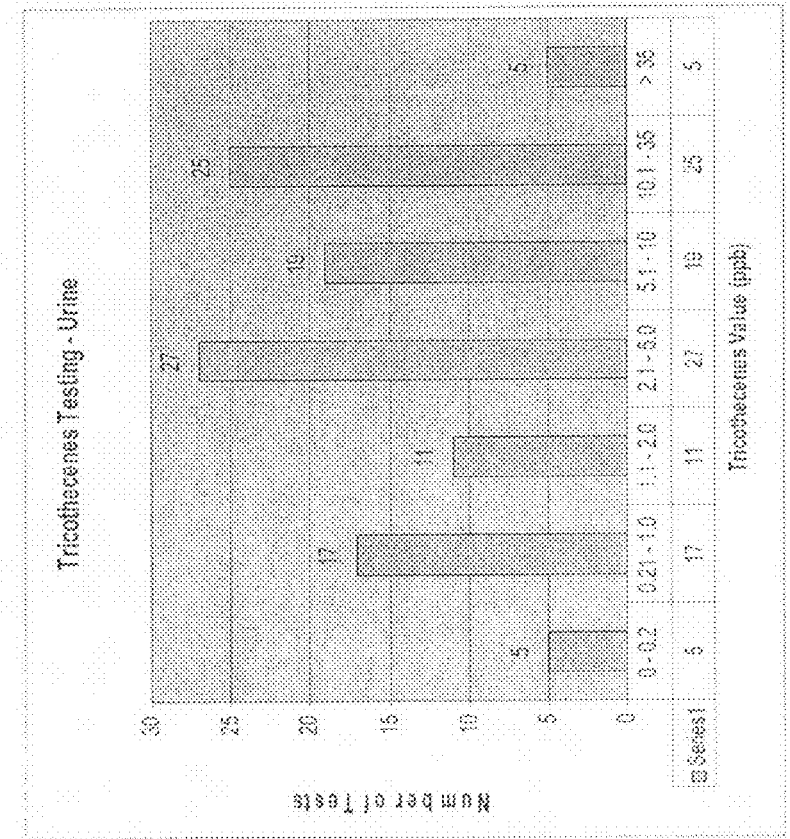
FIG. 1 shows Tricothecenes values for urine tests.

The present invention relates to methods and compositions for identifying or detecting the presence of molds (i.e., fungi) in patient tissue and body fluids. The identification and detection methods are based on 1.) amplification of fungal DNA using a PCR-based method and 2.) detection and quantification of mycotoxins in patient body fluids and tissues. The methods and compositions (e.g., primers and probes) for amplification of fungal DNA are highly specific and sensitive and avoid co-amplification of or do not co-amplify non-specific human or animal nucleic acids.

The methods and compositions for detection and quantification of mycotoxins are also very specific and sensitive. These methods and compositions utilize antibody-based identification of mycotoxins. In illustrative embodiments, Enzyme Linked Immunosorbant Assay (ELISA), or affinity chromatography can be used to detect mycotoxins produced by toxic molds. Illustratively, the mycotoxins can be aflatoxins, ochratoxins, or tricothecenes (e.g., Verrucarins A, B and J, Roridin A, E, H, and L-2, Satratoxins F, G, and H, Verrucarol, isosatratoxin F, G, and H, and T-2). Illustrative of antibody-based assays that can be used to identify mycotoxins are the Tricothecene kit (Envirologix, Inc., Portland, Me.), the AflaTest® (VICAM, Inc.), the OchraTest™ (VICAM Inc.), and Luminex®-based assays.

Aflatoxins are toxin metabolites produced by a variety of molds such as *Aspergillus flavus* and *Aspergillus parasiticus*. Aflatoxins are carcinogenic and can be present in grains, nuts, cottonseed and other commodities associated with human food or animal feeds. Crops may be contaminated by one or more of the four sub-types of aflatoxins, B1, B2, G1 and G2. Aflatoxin B1 is the most toxic and frequently detected aflatoxin. Aflatoxins have been implicated in human health disorders including hepatocellular carcinoma, Reye's syndrome, and chronic hepatitis.

Ochratoxin A is the most important and most commonly occurring of a structurally related group of compounds called ochratoxins. Ochratoxin A is produced by some species of *Aspergillus,* such as *A. ochraceus,* and by *Penicillium verrucosum*. Ochratoxin A is a potent toxin affecting mainly the kidneys, in which it can cause both acute and chronic lesions. A nephrotoxic effect has been demonstrated in all mammalian species, and both teratogenic and reproductive effects have been demonstrated. Ochratoxin A is known to affect the immune system in a number of mammalian species.

Some tricothecenes are macrocyclic mycotoxins. There are over one hundred trichothecenes that cause irritation and immunosuppressive effects (Ueno, Y. 1983 and Tuomi, et al. 2000). Most tricothecenes were originally isolated from species of *Fusarium,* but they also may be produced by other fungi, such as species of *Stachybotrys, Trichothecium,* and others (Kurata and Ueno, 1983 and Ueno, Y. 1983). *Stachybotrys chartarum* is known to produce a number of potent mycotoxins in this family including Verrucarins B and J, Roridin E, Satratoxins F, G, and H, and isosatratoxin F, G, and H (Hinkley, et al. 2001 and Jarvis, et al, 1998). These mycotoxins are also known to be potent inhibitors of protein synthesis in eukaryotes.

In various illustrative embodiments, body fluids that can be tested for the presence of fungal DNA or mycotoxins, include, but are not limited to, urine, nasal secretions, nasal washes, inner ear fluids, bronchial lavages, bronchial washes, alveolar lavages, spinal fluid, bone marrow aspirates, sputum, pleural fluids, synovial fluids, pericardial fluids, peritoneal fluids, saliva, tears, gastric secretions, stool, reproductive tract secretions, such as seminal fluid, lymph fluid, and whole blood, serum, or plasma. These samples can be prepared for testing as described herein. In various embodiments, tissue samples can include tissue biopsies of hospital patients or out-patients and autopsy specimens. As used herein, the term "tissue" includes, but is not limited to, biopsies, autopsy specimens, cell extracts, tissue sections, aspirates, tissue swabs, and fine needle aspirates.

In accordance with the invention the word "patient" means a human or an animal, such as a domestic animal (e.g., a dog or a cat). Accordingly, the methods and compositions disclosed herein can be used for both human clinical medicine and veterinary applications. Thus, the patient afflicted with a disease state related to a fungal infection can be a human, or in the case of veterinary applications, can be a laboratory, agricultural, domestic or wild animal. The present invention can be applied to patients including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, chickens, and wild animals in captivity such as bears, pandas, lions, tigers, leopards, elephants, zebras, giraffes, gorillas, dolphins, and whales.

The methods and compositions described herein can be used to detect or identify microbial DNA (e.g., fungal DNA) or microbial toxins (e.g., mycotoxins) in microbes selected from the group consisting of *Absidia coerulea, Absidia glauca, Absidia corymbifera, Acremonium strictum, Alternaria alternata, Apophysomyces elegans, Saksena vasiformis, Aspergillus flavus, Aspergillus oryzae, Aspergillus fumigatus, Neosartoryta fischeri, Aspergillus niger, Aspergillus foetidus, Aspergillus phoenicus, Aspergillus nomius, Aspergillus ochraceus, Aspergillus ostianus, Aspergillus auricomus, Aspergillus parasiticus, Aspergillus sojae, Aspergillus restrictus, Aspergillus caesillus, Aspergillus conicus, Aspergillus sydowii, Aspergillus tamarii, Aspergillus terreus, Aspergillus ustus, Aspergillus versicolor, Aspergillus ustus, Aspergillus versicolor, Chaetomium globosum, Cladosporium cladosporioides, Cladosporium herbarum, Cladosporium sphaerospermum, Conidiobolus coronatus, Conidiobolus incongruus, Cunninghamella elegans, Emericella nidulans, Emericella rugulosa, Emericilla quadrilineata, Apicoccum nigrum, Eurotium amstelodami, Eurotium chevalieri, Eurotium herbariorum, Eurotium rubrum, Eurotium repens, Geotrichum candidum, Geotrichum klebahnii, Memnoniella echinata, Mortierella polycephala, Mortierella wolfii, Mucor mucedo, Mucor amphibiorum, Mucor circinelloides, Mucor heimalis, Mucor indicus, Mucor racemosus, Mucor ramosissimus, Rhizopus azygosporous, Rhizopus homothalicus, Rhizopus microsporus, Rhizopus oligosporus, Rhizopus oryzae, Myrothecium verrucaria, Myrothecium roridum, Paecilomyces lilacinus, Paecilomyces variotii, Penicillium freii, Penicillium verrucosum, Penicillium hirsutum, Penicillium alberechii, Penicillum aurantiogriseum, Penicillium polonicum, Penicillium viridicatum, Penicillium hirsutum, Penicillium brevicompactum, Penicillium chrysogenum, Penicillium griseofulvum, Penicillium glandicola, Penicillium coprophilum, Eupenicillium crustaceum, Eupenicillium egyptiacum, Penicillium crustosum, Penicillium citrinum, Penicillium sartoryi, Penicillium westlingi, Penicillium corylophilum, Penicillium decumbens, Penicillium echinulatum, Penicillium solitum, Penicillium camembertii, Penicillium commune, Penicillium echinulatum, Penicillium sclerotigenum, Penicillium italicum, Penicillium expansum, Penicillium fellutanum, Penicillium charlesii, Penicillium janthinellum, Penicillium raperi, Penicillium madriti, Penicillium gladioli, Penicillium oxalicum, Penicillium roquefortii, Penicillium simplicissimum, Penicillium ochrochloron, Penicillium spinulosum, Penicillium glabrum, Penicillum thomii, Penicillium pupurescens, Eupenicillium lapidosum, Rhizomucor miehei, Rhizomucor pusillus, Rhizomucor variabilis, Rhizopus stolonifer, Scopulariopsis asperula, Scopulariopsis brevicaulis, Scopulariopsis fusca, Scopulariopsis brumptii, Scopulariopsis chartarum, Scopulariopsis sphaerospora, Trichoderma asperellum, Trichoderma hamatum, Trichoderma viride, Trichoderma harzianum, Trichoderma longibrachiatum, Trichoderma citroviride, Trichoderma atroviride, Trichoderma koningii, Ulocladium atrum, Ulocladium chartarum, Ulocladium botrytis, Wallemia sebi, Stachybotrys chartarum,* and the like.

In embodiments where the microbe is a fungal species, the microbe is typically selected from the group consisting of *S. chartarum, S. prolificans, A. versicolor, A. vesicularis, A. niger, P. chrysogenum, P. verrucosum, G. candidum, A. flavus, A. fumigatus, A. nidulans, A. ochraceus, A. paraciticus, A. sydowii, A. ustus, F. solani, F. chlamydosporum, P. aurantiogriseum, P. citrinum, P. corylophilum, P. crustosum, P. expansum, P. fellutanum, P. roquefortii, P. simplicissimum, S. echinata,* and *E. amstelodami.* In one embodiment, the molds (i.e., fungi) can be black, toxigenic molds.

In one illustrative embodiment, a method is provided of identifying a specific fungal species in patient tissue or body fluid. The method comprises the steps of extracting and recovering DNA of the fungal species from the patient tissue or body fluid, amplifying the DNA, hybridizing a probe to the DNA to specifically identify the fungal species, and specifically identifying the fungal species.

In some embodiments, real-time PCR-based methods can be used to amplify the fungal DNA and to detect and identify fungal DNA by hybridization of the probe to the fungal DNA. PCR is described in U.S. Pat. Nos. 4,683,202 and 4,800,159, incorporated herein by reference, and methods for PCR are well-known in the art. Real-time PCR combines amplification and simultaneous probe hybridization to achieve sensitive and specific detection of infectious molds (i.e., fungi) in real-time thereby providing instant detection of molds. In this embodiment, the time to detect or identify the fungus and to obtain a diagnosis is greatly reduced. Real-time PCR is conducted according to methods well-known in the art. Exemplary probes and primers and their target DNAs, that can be used in accordance with the invention are shown below. "Primer F" refers to a forward primer and "Primer R" refers to a reverse primer which are well-known terms in the art.

```
Target 1-S. chartarum
    Probe 1 char:    5'-ttgcttcggcgggaacgccccg    (SEQ ID NO: 1)

Primer F2:       5'-gcggagggatcattaccgag      (SEQ ID NO: 2)

Primer R2:       5'-atcgatgccagagccaagag      (SEQ ID NO: 3)

Target 2-A. versicolor
    Probe 2 vers:    5'-cggggagccctctcgggggc      (SEQ ID NO: 4)

Primer F1:       5'-cgtaggtgaacctgcggaag      (SEQ ID NO: 5)
```

-continued

```
Primer R1:        5'-atcgatgccggaaccaagag       (SEQ ID NO: 6)

Target 3-A. niger
Probe 3 niger:    5'-tgtctattgtacctgttgcttc     (SEQ ID NO: 7)

Primer F14:       5'-cgtaggtgaacctgcggaag       (SEQ ID NO: 8)

Primer R1:        5'-atcgatgccggaaccaagag       (SEQ ID NO: 9)

Target 4-P. chrysogenum
Probe 4 chry:     5'-ctctgtctgaagattgtagtctgagt (SEQ ID NO: 10)

Primer F1:        5'-cgtaggtgaacctgcggaag       (SEQ ID NO: 11)

Primer R1:        5'-atcgatgccggaaccaagag       (SEQ ID NO: 12)

Target 5-P. verrucosum
Probe 5 verru:    5'-cccgcctttgctggccgcc        (SEQ ID NO: 13)

Primer F1:        5'-cgtaggtgaacctgcggaag       (SEQ ID NO: 14)

Primer R1:        5'-atcgatgccggaaccaagag       (SEQ ID NO: 15)

Target 6-G. candidum
For Geo F1H:      5'-ggatctcttggttctcgtatc      (SEQ ID NO: 16)

Rev Geo R1H:      5'-cttgatctgaggttgaatagtg     (SEQ ID NO: 17)

Probe 6 geo:      5"-aacgcacattgcactttggggtatc  (SEQ ID NO: 18)

Target 7-A. flavus
Probe 7 flav:     5'-cccgccattcatggccgccggg     (SEQ ID NO: 19)

Primer F1:        5'-cgtaggtgaacctgcggaag       (SEQ ID NO: 20)

Primer R1:        5'-atcgatgccggaaccaagag       (SEQ ID NO: 21)

Target 8-A. fumigatus
Probe 8 fumi:     5'-aaagtatgcagtctgagttgattatc (SEQ ID NO: 22)

Primer F1:        5'-cgtaggtgaacctgcggaag       (SEQ ID NO: 23)

Primer R1:        5'-atcgatgccggaaccaagag       (SEQ ID NO: 24)

Target 9-A. nidulans
Probe 9 nid:      5'-cccaggggggcgagccgccgg       (SEQ ID NO: 25)

Primer F1:        5'-cgtaggtgaacctgcggaag       (SEQ ID NO: 26)

Primer R1:        5'-atcgatgccggaaccaagag       (SEQ ID NO: 27)

Target 10-A. ochraceus
Probe 10 ochr:    5'-acaccaacgtgaacactgtctgaag  (SEQ ID NO: 28)

Primer F1:        5'-cgtaggtgaacctgcggaag       (SEQ ID NO: 29)

Primer R1:        5'-atcgatgccggaaccaagag       (SEQ ID NO: 30)

Target 11-A. paraciticus
Probe 11 para:    5'-cgggcccgccgtcatggccg       (SEQ ID NO: 31)

Primer F1:        5'-cgtaggtgaacctgcggaag       (SEQ ID NO: 32)

Primer R1:        5'-atcgatgccggaaccaagag       (SEQ ID NO: 33)

Target 12-A. sydowii
Probe 12 syd:     5'-ccctcggggcgagccgccg        (SEQ ID NO: 34)

Primer F1:        5'-cgtaggtgaacctgcggaag       (SEQ ID NO: 35)

Primer R1:        5'-atcgatgccggaaccaagag       (SEQ ID NO: 36)

Target 13-A. ustus
Probe 13 ust:     5'-ccacaccgaacctcttgttatagc   (SEQ ID NO: 37)
```

-continued

```
Primer F1:      5'-cgtaggtgaacctgcggaag       (SEQ ID NO: 38)

Primer R1:      5'-atcgatgccggaaccaagag       (SEQ ID NO: 39)

Target 14-F. solani
Probe 14 salani: 5'-cgggaatagacggccccgtgaaac  (SEQ ID NO: 40)

Primer F2:      5'-gcggagggatcattaccgag       (SEQ ID NO: 41)

Primer R2:      5'-atcgatgccagagccaagag       (SEQ ID NO: 42)

Target 15-P. aurantiogriseum
Probe 15 auran: 5'-cccgcctttactggccgccgg     (SEQ ID NO: 43)

Primer F1:      5'-cgtaggtgaacctgcggaag       (SEQ ID NO: 44)

Primer R1:      5'-atcgatgccggaaccaagag       (SEQ ID NO: 45)

Target 16-P. citrinum
Probe 16 citr:  5'-tgttgcctcggcgggcccgc      (SEQ ID NO: 46)

Primer F4:      5'-ggaaggatcattaccgagtg       (SEQ ID NO: 47)

Primer R1:      5'-atcgatgccggaaccaagag       (SEQ ID NO: 48)

Target 17-P. corylophilum
Probe 17 corylo: 5'-ttattgtaccttgttgcttcggcgg (SEQ ID NO: 49)

Primer F1:      5'-cgtaggtgaacctgcggaag       (SEQ ID NO: 50)

Primer R1:      5'-atcgatgccggaaccaagag       (SEQ ID NO: 51)

Target 18-P. crustosum
Probe 18 crust: 5'-cgatctccgggggacgggcc      (SEQ ID NO: 52)

Primer F7:      5'-ctgtccgagcgtcattgctg       (SEQ ID NO: 53)

Primer R5:      5'-cgaggaccggacgcggtg         (SEQ ID NO: 54)

Target 19-P. expansum
Probe 19 expan: 5'-agacaccccgaactctgcctgaa   (SEQ ID NO: 55)

Primer F1:      5'-cgtaggtgaacctgcggaag       (SEQ ID NO: 56)

Primer R1:      5'-atcgatgccggaaccaagag       (SEQ ID NO: 57)

Target 20-P. fellutanum
Probe 20 fell:  5'-cccgcctgccaggccgccg       (SEQ ID NO: 58)

Primer F1:      5'-cgtaggtgaacctgcggaag       (SEQ ID NO: 59)

Primer R1:      5'-atcgatgccggaaccaagag       (SEQ ID NO: 60)

Target 21-P. roquefortii
Probe 21 roque: 5'-cacccgtgtttatttaccttattgc (SEQ ID NO: 61)

Primer F1:      5'-cgtaggtgaacctgcggaag       (SEQ ID NO: 62)

Primer R1:      5'-atcgatgccggaaccaagag       (SEQ ID NO: 63)

Target 22-P. simplicissimum
Probe 22 simpl: 5'-cacccgtgtttatcgtaccttgttg (SEQ ID NO: 64)

Primer F1:      5'-cgtaggtgaacctgcggaag       (SEQ ID NO: 65)

Primer R1:      5'-atcgatgccggaaccaagag       (SEQ ID NO: 66)

Target 23-S. echinata
Probe 23 echin: 5'-ttgcttcggcgggagagccccg    (SEQ ID NO: 67)

Primer F2:      5'-gcggagggatcattaccgag       (SEQ ID NO: 68)

Primer R2:      5'-atcgatgccagagccaagag       (SEQ ID NO: 69)

Target 24-E. amstelodami
Probe 24 amst:  5'-tgtctatctgtaccctgttgcttcg (SEQ ID NO: 70)

Primer F1:      5'-cgtaggtgaacctgcggaag       (SEQ ID NO: 71)
```

```
Primer R1:            5'-atcgatgccggaaccaagag      (SEQ ID NO: 72)

Fungal Universal Group 1
UP1:                  5'-cctcggatcaggtagggatac     (SEQ ID NO: 73)

UF1:                  5'-atgcctgtccgagcgtcatt      (SEQ ID NO: 74)

UR1:                  5'-ttcctccgcttattgatatg      (SEQ ID NO: 75)

Fungal Universal Group 2
Up2:                  5'-acggatctcttggctctggcatc   (SEQ ID NO: 76)

F2:                   5'-gcggagggatcattaccgag      (SEQ ID NO: 77)

UR2:                  5'-ttcactgaattctgcaattcac    (SEQ ID NO: 78)
```

Alternative illustrative embodiments for the Target 3 probe and primer F1 are 5'-cctctgccccccgggcccgtg (SEQ ID NO: 79) and 5'-ggaaggatcattaccgagtg (SEQ ID NO: 80), respectively. An alternative illustrative embodiment for the Target 9 probe is 5'-ggagcccccagggggcgag (SEQ ID NO: 81). An alternative illustrative embodiment for the Target 12 probe is 5'-cggggaaccccctcggggc (SEQ ID NO: 82). An alternative illustrative embodiment for the Target 13 probe is 5'-tgcgctccccccgggggcag (SEQ ID NO: 83). Alternative illustrative embodiments for the Target 18 probe, primer F7, and primer R5 are 5'-ggccccgtcccccgatctccg (SEQ ID NO: 84), 5'-agtgaatcatcgagtctttgaac (SEQ ID NO: 85), and 5'-acctgatccgaggtcaacctg (SEQ ID NO: 86), respectively. An alternative illustrative embodiment for the Target 20 probe is 5'-cgggcccgcctgccaggccg (SEQ ID NO: 87). An alternative illustrative embodiment for the Target 21 probe is 5'-ccggggggtttacaccccg (SEQ ID NO: 88). An alternative illustrative embodiment for the Target 22 probe is 5'-ccggggggcatctgccccgg (SEQ ID NO: 89).

In various embodiments, sample preparation (i.e., preparation of the target DNA) involves rupturing the cells (e.g., cells of the tissue or fungal spores in patient body fluid or tissue) and isolating the fungal DNA from the lysate. Techniques for rupturing cells and for isolation of DNA are well-known in the art. For example, cells may be ruptured by using a detergent or a solvent, such as phenol-chloroform. DNA may be separated from the lysate by physical methods including, but not limited to, centrifugation, pressure techniques, or by using a substance with affinity for DNA, such as, for example, silica beads. After sufficient washing, the isolated DNA may be suspended in either water or a buffer. In other embodiments, commercial kits are available, such as Quiagen™, Nuclisensm™, and Wizard™ (Promega), and Promegam™. Methods for isolating DNA are described in Sambrook et al., "Molecular Cloning: A Laboratory Manual", 3rd Edition, Cold Spring Harbor Laboratory Press, (2001), incorporated herein by reference.

In various embodiments described herein, the primers and probes used for amplification of the target DNA and for detection and identification of fungal DNA are oligonucleotides from about ten to about one hundred, more typically from about ten to about thirty or about six to about twenty-five base pairs long, but any suitable sequence length can be used. In illustrative embodiments, the primers and probes may be double-stranded or single-stranded, but the primers and probes are typically single-stranded. The primers and probes described herein are capable of specific hybridization, under appropriate hybridization conditions (e.g., appropriate buffer, ionic strength, temperature, formamide, and $MgCl_2$ concentrations), to a region of the target DNA. The primers and probes described herein are designed based on having a melting temperature within a certain range, and substantial complementarity to the target DNA. Methods for the design of primers and probes are described in Sambrook et al., "Molecular Cloning: A Laboratory Manual", 3rd Edition, Cold Spring Harbor Laboratory Press, (2001), incorporated herein by reference.

The primers and probes described herein for use in PCR can be modified by substitution, deletion, truncation, and/or can be fused with other nucleic acid molecules wherein the resulting primers and probes hybridize specifically to the intended targets and are useful in the methods described herein for amplification of the target DNAs. Derivatives can also be made such as phosphorothioate, phosphotriester, phosphoramidate, and methylphosphonate derivatives, that specifically bind to single-stranded DNA or RNA (Goodchild, et al., Proc. Natl. Acad. Sci. 83:4143-4146 (1986)).

The invention encompasses isolated or substantially purified nucleic acids. An "isolated" or. "purified" nucleic acid molecule is substantially free of other cellular material, or culture medium when produced by recombinant techniques, or substantially free of chemical precursors or other chemicals when chemically synthesized. Preferably, an "isolated" or "purified" nucleic acid is free of sequences that naturally flank the nucleic acid in the genomic DNA of the organism from which the nucleic acid is derived. For example, in various embodiments, the isolated or purified nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

Also within the scope of the invention are nucleic acids complementary to the probes and primers described herein, and those that hybridize to the nucleic acids described herein or those that hybridize to their complements under highly stringent conditions. In accordance with the invention "highly stringent conditions" means hybridization at 65° C. in 5× SSPE and 50% formamide, and washing at 65° C. in 0.5× SSPE. Conditions for low stringency and moderately stringent hybridization are described in Sambrook et al., "Molecular Cloning: A Laboratory Manual", 3rd Edition, Cold Spring Harbor Laboratory Press, (2001), incorporated herein by reference. In some illustrative aspects, hybridization occurs along the full-length of the nucleic acid.

Also included are nucleic acid molecules having about 60%, about 70%, about 75%, about 80%, about 85%, about 90%, about 95%, 96%, 97%, and 98% homology to the probes and primers described herein. Determination of percent identity or similarity between sequences can be done, for example, by using the GAP program (Genetics Computer Group, software; now available via Accelrys on http://www.accelrys.com), and alignments can be done using, for example, the ClustalW algorithm (VNTI software, InforMax Inc.). A sequence database can be searched using the nucleic acid sequence of interest. Algorithms for database searching are typically based on the BLAST software (Altschul et al., 1990). In some embodiments, the percent identity can be determined along the full-length of the nucleic acid.

As used herein, the term "complementary" refers to the ability of purine and pyrimidine nucleotide sequences to associate through hydrogen bonding to form double-stranded nucleic acid molecules. Guanine and cytosine, adenine and thymine, and adenine and uracil are complementary and can associate through hydrogen bonding resulting in the formation of double-stranded nucleic acid molecules when two nucleic acid molecules have "complementary" sequences. The complementary sequences can be DNA or RNA sequences. The complementary DNA or RNA sequences are referred to as a "complement."

Techniques for synthesizing the probes and primers described herein are well-known in the art and include chemical syntheses and recombinant methods. Such techniques are described in Sambrook et al., "Molecular Cloning: A Laboratory Manual", 3rd Edition, Cold Spring Harbor Laboratory Press, (2001), incorporated herein by reference. Primers and probes can also be made commercially (e.g., CytoMol, Sunnyvale, Calif. or Integrated DNA Technologies, Skokie, Ill.). Techniques for purifying or isolating the probes and primers described herein are well-known in the art. Such techniques are described in Sambrook et al., "Molecular Cloning: A Laboratory Manual", 3rd Edition, Cold Spring Harbor Laboratory Press, (2001), incorporated herein by reference. The primers and probes described herein can be analyzed by techniques known in the art, such as restriction enzyme analysis or sequencing, to determine if the sequence of the primers and probes is correct.

In various embodiments of the methods and compositions described herein, the probes and primers can be labeled, such as with fluorescent compounds, radioactive isotopes, antigens, biotin-avidin, colorimetric compounds, or other labeling agents known to those of skill in the art, to allow detection and quantification of amplified DNA, such as by Real-Time PCR. In illustrative embodiments, the labels may include 6-carboxyfluorescein (FAM™), TET™ (tetrachloro-6-carboxyfluorescein), JOE™ (2,7,-dimethoxy-4,5-dichloro-6-carboxyfluorescein), VIC™, HEX (hexachloro-6-carboxyfluorescein), TAMRA™ (6-carboxy-N,N,N',N'-tetramethylrhodamine), BHQ™, SYBR® Green, Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein, Oregon Green 488, Oregon Green 500, Oregon Green 514, Pacific Blue, REG, Rhodamine Green, Rhodamine Red, ROX, and/or Texas Red.

Specificity of the probes and primers described herein was demonstrated by testing hybridization of the probe and primers sets against 23 different mold organisms (10 species of Aspergillus, 10 species of Penicillium, 2 species of Stachybotryous, and 1 specie of Fusarium). There were no cross-over reactions or cross-over detection noted for any of the tested probe and primer sequences. Thus, the methods and compositions (e.g., primers and probes) for amplification of fungal DNA are highly specific and avoid co-amplification of or do not co-amplify non-specific nucleic acids.

In one illustrative embodiment, universal probes can be used to provide a method for determining the presence of fungal DNA before conducting target-specific assays. In one embodiment, universal probes and primers can be used to detect the presence of Aspergillus and Penicillium species (see probes and primers for Fungal Universal Group 1 below).

In another embodiment, universal probes and primers can be used to detect the presence of Stachybotrys and Fusarium species (see probes and primers for Fungal Universal Group 2 below). In these embodiments, the probes and primers can be homologous for all targets of interest related to Aspergillus, Penicillium, Stachybotrys, and Fusarium species.

| Fungal Universal Group 1 | |
|---|---|
| UP1: 5'-cctcggatcaggtagggatac | (SEQ ID NO: 73) |
| UF1: 5'-atgcctgtccgagcgtcatt | (SEQ ID NO: 74) |
| UR1: 5'-ttcctccgcttattgatatg | (SEQ ID NO: 75) |
| Fungal Universal Group 2 | |
| Up2: 5'-acggatctcttggctctggcatc | (SEQ ID NO: 76) |
| F2: 5'-gcggagggatcattaccgag | (SEQ ID NO: 77) |
| UR2: 5'-ttcactgaattctgcaattcac | (SEQ ID NO: 78) |

In another illustrative embodiment, a method is provided of identifying a mycotoxin in patient tissue or body fluid. The method comprises the steps of extracting and recovering the mycotoxin from the patient tissue or body fluid, contacting the mycotoxin with an antibody directed against the mycotoxin, and identifying the myocotoxin.

Illustratively, patient (e.g., human or animal) tissue is received in 1.) a 10% formalin fluid or 2.) in a paraffin block in which the tissue has been fixed in formalin. In one embodiment for mycotoxin detection and quantitation, the tissue can then be processed by various dehydration steps and finally embedded in paraffin. In this embodiment, the tissue can then be cut in 3-5 micron samples. In an illustrative embodiment, approximately 25-35 mg of tissue can then be processed as described in Examples 2-6 for mycotoxin extraction. Illustratively, body fluids can be prepared as described in Examples 1 and 3-6 or by other methods known in the art. In another illustrative embodiment, patient body fluids can be tested for the presence of mycotoxins. Illustratively, any antigen associated with a fungus or with a mycotoxin can be detected.

The methods and compositions for detection and quantification of mycotoxins are very specific and sensitive (e.g., sensitivity of 1.0 ng/ml for aflatoxins, 0.2 ng/ml for Tricothecenes, and 2 ng/ml for ochratoxins). Specificity of mycotoxins was tested in each group (Tricothecenes, Aflatoxins, Ochratoxins) by testing known samples of mycotoxins (obtained from Trilogy Laboratories, Washington, Mo., and from Sigma, St. Louis, Mo.) in each mycotoxin test. There were no cross-over reactions or cross-over detection of mycotoxins between the groups. Thus, the methods and compositions for detection and quantification of mycotoxins are also very specific and sensitive. The methods and compositions described in Examples 2-6 utilize antibody-based identification of mycotoxins. In illustrative embodiments, Enzyme-Linked Immunosorbant Assay (ELISA), affinity chromatography, or a Luminex®-based assay can be used to detect mycotoxins produced by toxic molds. Illustratively, the mycotoxins can be aflatoxins, ochratoxins, or Tricothecenes (e.g., Verrucarins A, B and J, Roridin A, E, H, and L-2, Satratoxins F, G, and H, Verrucarol, isosatratoxin F, G, and H, and T-2).

Illustrative of antibody-based assays that can be used to identify and subsequently quantitate mycotoxins, or fungal or mycotoxin antigens, are the Tricothecene kit (Envirologix, Inc., Portland, Me.), the AflaTest® (VICAM, Inc.), and the OchraTest™ (VICAM Inc., Watertown, Mass.).

Another exemplary detection method for multiple mycotoxins in patient samples that have been exposed to fungal targets belonging to, for example, *Aspergillus, Penicillium, Stachybotrys,* and *Fusarium* species is the Luminex® format (Luminex, Austin, Tex., see Examples 9 and 11-13). In one aspect of the invention, the Luminex® assay utilizes microspheres (beads) that are dyed with fluorochromes and that are coupled to antigens to detect antibodies, in patient body fluids or tissues, to mycotoxins, mycotoxin antigens, or other fungal antigens. In another embodiment, the microspheres are coupled to antibodies to detect, in patient body fluids or tissues, mycotoxins, mycotoxin antigens, or other fungal antigens. In this illustrative embodiment, the antibodies coupled to the microspheres can be polyclonal or monoclonal antibodies, but monoclonal antibodies are typically used. In another illustrative embodiment, the beads can be coupled to DNA probes to detect DNA specific to fungal species. Exemplary methods involving the Luminex® assay are described in more detail in Examples 9 and 11-13.

In the embodiment where mycotoxins are identified and quantitated, control samples of the body fluid or tissue to be analyzed can be obtained from patients with no documented history of exposure to molds or mycotoxins. For example, negative control samples can be obtained from autopsy specimens in which the patient had no exposure to mycotoxins or molds (e.g., victims of motor vehicle accidents, coronary artery disease, or myocardial infarction). For positive controls, for example, samples of negative tissue and/or body fluids can be spiked with known positive amounts of mycotoxins or spores prior to evaluation to generate a calibration curve (see Examples 4-6). Illustrative calibrators for the mycotoxins can be obtained from producers of the Tricothecene kit (Envirologix, Inc., Portland, Me.) and producers of the AflaTest® and OchraTest™ kits (VICAM Inc., Watertown, Mass.), or from Trilogy Laboratories (Washington, Mo.).

In another embodiment, a method is provided of determining if a patient is at risk for or has developed a disease state related to a fungal infection. The method comprises the steps of extracting and recovering a mycotoxin (i.e., a mycotoxin or a mycotoxin antigen) from a tissue or body fluid of the patient, contacting the mycotoxin (i.e., a mycotoxin or a mycotoxin antigen) with an antibody directed against the toxin, identifying the mycotoxin (i.e., a mycotoxin or a mycotoxin antigen), and determining if the patient is at risk for or has developed the disease state related to the fungal infection. In another embodiment, a method is provided of determining if a patient is at risk for or has developed a disease state related to a fungal infection. The method comprises the steps of extracting and recovering DNA of a specific fungal species from a tissue or body fluid of the patient, amplifying the DNA, hybridizing a probe to the DNA to specifically identify the fungal species, and specifically identifying the fungal species.

In any embodiment involving "determining if the patient has developed the disease state related to the fungal infection," this phrase means "diagnosing the patient with a fungal infection." The method embodiments described in the preceding paragraph provide methods of diagnosing fungal infections. Patients in need of diagnosis of a fungal infection can include cancer patients, post-operative patients, transplant patients, patients undergoing chemotherapy, immunosuppressed patients, and the like. These patients may experience symptoms of fungal infections including sinusitis, allergic reactions, headaches, and skin rashes. Patients in need of diagnosis may include humans or animals.

In one embodiment, for diagnosing fungal infections, kits are provided. The kits are useful for identifying, detecting, or quantitating fungal DNA or mycotoxins in a patient tissue or body fluid. In the embodiment where the kit is used to identify fungal DNA, the kit can contain the probes and/or primers described herein, components to extract and isolate fungal DNA, and components for DNA amplification, such as a heat stable DNA polymerase (e.g., Taq polymerase or Vent polymerase), buffers, $MgCl_2$, $H_2O$, and the like. In the embodiment where the kit is used to identify mycotoxins (i.e., a mycotoxin or a mycotoxin antigen), the kit can contain components to extract and isolate the mycotoxin (i.e., a mycotoxin or a mycotoxin antigen), antibody affinity matrices, ELISA plates, Luminex® beads, polyclonal or monoclonal antibodies, color development reagents, buffers, and the like. In one embodiment, the reagents can remain in liquid form. In another embodiment, the reagents can be lyophilized. In another illustrative embodiment, the kit can be used to detect other fungal antigens. The kits can also contain instructions for use.

In another embodiment, a kit comprising a purified nucleic acid with a sequence selected from the group consisting of SEQ ID NO: 1 to SEQ ID NO: 89 or a complement of a sequence selected from the group consisting of of SEQ ID NO: 1 to SEQ ID NO: 89 is provided. The kit can comprise components for the extraction and recovery of fungal DNA or a mycotoxin from the body fluid or tissue of a patient. The kit can further comprise components for identification of the fungal DNA or the mycotoxin. The components for identification of the fungal DNA or the mycotoxin can include beads dyed with a fluorochrome and coupled to a probe for the fungal DNA or to antibodies to the mycotoxin or to the mycotoxin itself or to a mycotoxin antigen.

A purified nucleic acid is also provided comprising a sequence of SEQ ID NO: 1 to SEQ ID NO: 89 or a sequence that hybridizes under highly stringent conditions to a sequence consisting of SEQ ID NO: 1 to SEQ ID NO: 89. A purified nucleic acid is also provided comprising a complement of a sequence of SEQ ID NO: 1 to SEQ ID NO: 89 or a sequence that hybridizes under highly stringent conditions to the complement of a sequence consisting of SEQ ID NO: 1 to SEQ ID NO: 89. In accordance with the invention "highly stringent conditions" means hybridization at 65° C. in 5× SSPE and 50% formamide, and washing at 65° C. in 0.5× SSPE.

A calibration reagent (or multiple calibration reagents) can also be included in the mycotoxin kit and "calibration reagent" means any standard or reference material containing a known amount of the mycotoxin (i.e., a mycotoxin or a mycotoxin antigen). The sample suspected of containing the mycotoxin and the calibration reagent (or multiple calibration reagents) are assayed under similar conditions. The mycotoxin concentration is then calculated by comparing the results obtained for the unknown sample with the results obtained for the calibration reagent(s).

The following examples provide illustrative methods for carrying out the practice of the present invention. As such, these examples are provided for illustrative purposes only and are not intended to be limiting.

EXAMPLE 1

Samples and Sample Preparation

Human urine was received in 5-10 ml quantities as first in the morning voided urines. Serums were received with the blood clot removed prior to receipt and a minimum of 1 ml of serum was frozen or used. Nasal secretions were obtained from hospital patients or out-patients. Fixed autopsy and surgical biopsy specimens were obtained from patients who had a history of exposure to mycotoxins or fungi. These samples were obtained from hospital pathology departments or coroners' offices. Tissue samples and body fluid samples were also obtained from patients who had no exposure to mycotoxins or fungi and were sampled as a negative control group. Tissue specimens were cut using procedures described in Examples 2 and 7.

All specimens were placed into two groups. Group 1 comprised samples from individuals with no reported symptoms or known fungi or mycotoxin exposure. These samples served as negative controls and n values differed in each group of specimens sampled. Group 2 comprised samples from individuals with reported exposure to non-identified fungi or chemicals. Each test conducted had a different n value. Common symptoms of patients corresponding to group 2 samples included blurred vision, memory loss, fatigue, headache, nausea, loss of balance, cognitive deficits, rhinitis, sinusitis, rashes, and allergies. A detailed history and symptoms were provided to correspond to each patient sample.

Human urine was tested for the mycotoxins Aflatoxin B1, B2, G1, and G2, Ochratoxin A, and Tricothecenes. The studies described herein demonstrated that higher levels of mycotoxins were detected in early a.m. samples. Nasal secretions and washings were obtained by injection of 3-5 ml of sterile saline in each nostril of a patient. The patient was instructed to hold the saline in the nostrils for 30 seconds and then blow the saline into a sterile container held close to the nose. The specimen(s) were then collected and placed in containers.

Negative control samples of mycotoxins were made by dilution techniques for Aflatoxin (Sigma), Ochratoxin (Sigma) and Roridin A (for Tricothecenes). Samples of extracted and filtered human heart tissue, liver tissue, urine, and nasal secretions (including sputum) were spiked with various levels of the above named toxins. Each time a sample was evaluated, calibrators and negative and positive spiked tissues and fluids were also evaluated. Statistical analysis on all types of samples for mycotoxins were performed for sensitivity and specificity.

EXAMPLE 2

Preparation of Tissues for Mycotoxin Extraction

Preparation of tissues for myctotoxin extraction from formalin fixed tissue and paraffin-embedded tissue from humans or animals was accomplished using the following procedure.
Specimens
Tissue was received as either tissue fixed in a 10% formalin solution or in a paraffin-embedded tissue block. Tissue can be stored indefinitely in either form. However, because of cross-linking of formalin and proteins which may give false negative readings for DNA, the tissue was not stored in formalin for greater than 6 months. A minimum of 25-35 mg of formalin-fixed tissue was required for mycotoxin extraction. A maximum of 3 grams of formalin-fixed tissue can be used.
Materials
Phosphate Buffered Saline (PBS; 0.9%), acid-washed silica beads (Cat # G1277; obtained from Sigma-Aldrich), collection tubes (2 ml) screw cap, methanol (reagent grade, Sigma), and microcentrifuge tubes (2 ml) were used.
Procedure
For silica beads, 0.3 g±0.01 g of silica bead beating glass was added to a 2 ml screw cap tube making sure that there were no glass beads in the cap or around the rim. The tubes containing the beads were sterilized in an autoclave on the dry cycle for 10 minutes. If a large amount of tissue was evaluated, the tissue was placed in a blender and blended in PBS until well emulsified in the PBS. The sample was then filtered using simple gravity filtration through Whatman #9 filter paper.

The samples were recorded and assigned numbers in a sample log. 25-35 mg of paraffin-embedded tissue was then weighed and placed in a 2.0 ml screw cap tube. Methanol was added (1.0 ml reagent grade methanol) to the tube with the 0.3 g of silica beads and the sample was vortexed for 1 minute. The samples were bead beated on the bead beater for 1 minute at the speed of 45. Then 500 µl of sample was removed and placed in 4.5 ml of PBS taking care not to remove the paraffin from the sample tube. The sample could then be used for extraction or could be frozen at −20 degrees centigrade to be used later in extraction and detection of aflatoxins, ochratoxins, and tricothecenes (see Examples 3-6).

EXAMPLE 3

Preparation of Body Fluids for Mycotoxin Detection

Urine was received from a morning fresh first-voided specimen and stored at 1-6 degrees centigrade in a glass container. A urine analysis was conducted using a dipstick to measure pH, specific gravity, glucose, nitrates, ketones, and blood. The urine was examined for sediment and was centrifuged at 2500 rpm for 5 minutes if sediment was present. The supernatant was saved in a glass container for mycotoxin testing (storing in plastic was avoided to avoid a decrease in the detection level of tricothecenes). The urine was then used as indicated in Example 4 for aflatoxin determination, Example 5 for ochratoxin determination, and Example 6 for tricothecene determination.

Nasal secretions and mucous samples as well as washes were observed for mucous presence. If mucous was present, a solution of MUCOSOL™ (Alpha Tec Systems, Inc. Vancouver, Wash.) was prepared and added in equal amounts of body fluid to MUCOSOL™ in the secretions containing mucous. The specimen was then allowed to incubate 30 minutes at room temperature. The specimen was then centrifuged and the supernatant was removed. The sediment was then re-suspended in 10 ml of PBS. The specimen was then treated like any other body fluid and subjected to tests as described in Examples 4, 5, and 6. If testing for the presence of fungal DNA was desired, the specimen was then subjected to the tests described in Example 7.

Blood samples were obtained from the negative control group and exposed patients. Specimens were allowed to clot (no anticoagulant added) and then centrifuged for 10 minutes at 2000 rpm. Specimens were stored at 1-6 degrees centigrade for 48 hours or were frozen at -20 degrees centigrade for an indefinite period of time. Blood samples were extracted in a manner similar to that described by Garbis et al., *Anal. Chem.* 73:53589-64 (2001) and Hedman et al. *Arch. Tieremahr.* 50:13-24 (1997). Serum samples were aliquoted in 200 µl amounts into sterile 1.5 ml polystyrene microcentrifuge tubes. Immediately, 600 µl of high performance HPLC grade acetonitrile (Fisher Scientific, Hampton, N.H.) was added. After 15 minutes, the samples were vortexed and centrifuged. The supernatants were transferred into clean 1.5 ml glass vials. Each sample was evaporated under a gentle stream of dry nitrogen and re-suspended in 100 µl of pre-warmed sterile water. This was the final working solution for ELISA assays.

Spinal fluid samples were analyzed as obtained from human patients. Samples were not processed before analysis.

EXAMPLE 4

Detection of Aflatoxins in Body Fluids and Tissues

Aflatoxins are mycotoxins produced by the fungus *Aspergillus*. Samples from body fluids and tissues were prepared as described in Examples 2 and 3. Samples were then applied to an AflaTest® column (VICAM, L.P., Watertown, Mass.) which contains specific monoclonal antibodies directed against Aflatoxins B 1, B2, G1, and G2. The aflatoxins bind to the antibodies on the column. The column was then washed to remove the immunoaffinity column of impurities. By passing an eluting solution through the column, the aflatoxin was removed from the antibody. The eluting solution was then read in a fluorometer. Aflatoxins B1, B2, G1, and G2 were detected using AflaTest® (VICAM, L.P., Watertown, Mass.) which is a well-known quantitative method for the detection of aflatoxins in grains and foodstuffs. This assay permits the measurement of all of the major aflatoxins (including B1, B2, G1, G2 and M1) without the use of toxic solvents (i.e., chloroform or methylene chloride).

In more detail, the procedure for body fluids and tissues was as follows. Tissue samples were prepared from fixed and paraffin-embedded tissues as described in Example 2 and body fluid samples were prepared as described in Example 3. One ml of the extracted tissue sample or body fluid was mixed with 10 ml of purified molecular grade water. The 10 ml of sample was then placed over an Aflatoxin® column (VICAM) and was filtered through the affinity column at a rate of 1-2 drops/second until air came through the column. Ten ml of an 80:20 solution of methanol:water was then passed through the column at a rate of 2 drops/second. Another 10 ml of purified water was passed through the affinity column at 2 drops/second. As an alternative procedure, ten ml of molecular grade water can be passed through the column at a rate of 2 drops/second. The affinity column was then eluted by passing 1.0 ml of HPLC grade methanol through the column at a rate of 1-2 drops/second and collecting all of the sample eluate (1 ml) in a glass cuvette. One ml of AflaTest® Developer (described below) containing bromine was added to the eluate in the cuvette. The specimen was then mixed well and the cuvette was placed in a calibrated fluorometer (Sequoia-Turner Model 450). The aflatoxin concentration was read after 60 seconds.

Preparation of AFLATEST® Developer Solution: Five ml of AflaTest® Developer concentrate solution (VICAM) was measured and placed in a 2 ounce amber glass bottle of a 50 ml bottle dispenser for the developer (VICAM Cat. no. 20600). Fourty-five ml of purified water was added and mixed. The developer solution should be used within 8 hours after preparation. To ensure that the developer and water show no fluorescence, 1.0 ml of each was placed in the fluorometer and read after 60 seconds. Results of the readings should be 0 ppb. Also, methanol blanks and purified water blanks should be read as 0 ppb. The results of the test were recorded in parts per billion (nanograms/mililiter).

Fluorometer Calibration: The Sequoia-Turner Fluorometer, Model 450, was calibrated as defined by the manufacturer's guidelines (VICAM). The machine was calibrated using standards supplied by VICAM (Green Standard=-2, and Red Standard=22). Known standards of Aflatoxin B1, B2, G1, and G2 were used (Trilogy Laboratories, Washington, Mo.). Standard Calibrators were made at 52 ppb, 26 ppb, and 2.6 ppb.

Pump and Set Up: AflaTest® affinity chromatography was performed with the AflaTest® affinity column attached to a pump stand. The stand has a glass syringe barrel that serves as a reservoir for the column. A large plastic syringe with tubing and coupling provides air pressure to manually push liquids through the column. An adjustable air pump (VICAM Cat. no. 20650) can be attached to the pump tube instead of the large pump syringe barrel to operate without using hand pressure. Four and six position pump stands with aquarium pumps (VICAM cat. no. 21045) were used when testing multiple specimens.

| AFLATOXIN PANEL RESULTS: AFLATOXIN PANEL | | | |
|---|---|---|---|
| Specimen | 0-0.5 ppb | >0.5 ppb | # of Tests |
| CSF | 2 | 0 | 2 |
| Nasal Secretions | 19 | 4 | 23 |
| Tissue Block | 6 | 3 | 9 |
| Urine | 9 | 24 | 33 |
| Other | 3 | 0 | 3 |
| Total: | 39 | 31 | 70 |

EXAMPLE 5

Detection of Ochratoxins in Body Fluids and Tissues

Ochratoxin A (OA) is detected using OchraTest® (VICAM, L.P., Watertown, Mass.) which is a well-known quantitative method for the detection of OA. This assay permits the measurement of the major OA without the use of toxic solvents (i.e., chloroform or methylene chloride). Ochratoxin is a mycotoxin produced by the fungus *Aspergillus ochraceous* and also by several species of *Penicillium* fungi. To measure ochratoxin levels, samples from body fluids and tissues are prepared by subjecting samples to the treatments described in Examples 2 and 3. The extracts are then applied to the OchraTest® column, which contains specific monoclonal antibodies for OA. The ochratoxin binds to the antibodies on the column. The column is then washed to remove impurities from the immunoaffinity column. By passing an eluting solution through the column, the ochratoxin is removed from the antibody. The eluting solution can then be measured in a fluorometer.

In more detail, the procedure for body fluids and tissues was as follows. Tissue samples were prepared from fixed and paraffin-embedded tissues as described in Example 2 and body fluid samples were prepared as described in Example 3. One ml of the extracted tissue sample, prepared sinus washes, or prepared urine was then mixed with 10 ml of PBS. The 10 ml of sample was then placed over an OchraTest® column (VICAM) and filtered through the affinity column at a rate of 1-2 drops/second until air came through the column. As an alternative procedure, 1.0 ml of sample can be mixed with 1.0 ml of 80:20 HPLC Grade Methanol: water solution. Then one (1) ml of the sample +80:20 HPLC Methanol: water solution can be added to 10 mls of PBS in each immunoaffinity column (OchraTest® column (VICAM)) and filtered through the affinity column at a rate of 1-2 drops/second until air came through the column. Ten ml of an 80:20 solution of methanol: water was then passed through the column at a rate of 2 drops/second. Ten ml of PBS was then passed through the affinity column at 2 drops/second. For the alternative procedure, these last two steps are not done. The affinity column was then washed by passing 10 ml of 1× Mycotoxin Wash Buffer (OchraTest® VICAM) through the column at a rate of 1-2 drops/second until air came through the column. The affinity column was then eluted by passing 1.5 ml of OchraTest® eluting solution through the column at a rate of 1 drop/second and collecting all of the sample eluate (1.5 ml) in a glass cuvette. The sample was mixed well and the cuvette was placed immediately into the calibrated fluorometer (Sequoia-Turner Model 450). The sample was read after 60 seconds. The results of the test are recorded in parts per billion (nanograms/mililiter).

Fluorometer Calibration: The Sequoia-Turner Fluorometer, Model 450, was calibrated as defined by the manufacturer's guidelines (VICAM). The machine was calibrated using standards supplied by VICAM (Green Standard=−1.5 and Red Standard=23; Mycotoxin Calibration Standards (1 vial each of 3 levels) were used). Standards were prepared from controls purchased from Trilogy Laboratories (Missouri). Standards were 50 ppb, 25 ppb, and 2.5 ppb. The lower limit of detection was determined to be 2.0 ppb using calibrators and known recovery rates of samples from the VICAM Immunoaffinity columns.

Pump and Set Up: OchraTest™® affinity chromatography was performed with the OchraTest™ affinity column attached to a pump stand. The stand has a glass syringe barrel that serves as a reservoir for the column. A large plastic syringe with tubing and coupling provides air pressure to manually push liquids through the column. An adjustable air pump (VICAM Cat. no. 20650) can be attached to the pump tube instead of the large pump syringe barrel to operate without using hand pressure. Four and six position pump stands with aquarium pumps (VICAM Cat. No. 21045) are used when testing multiple specimens.

| OCHRATOXIN PANEL | | | |
|---|---|---|---|
| Specimen | 0-2.0 ppb | >2.0 ppb | # of Tests |
| CSF | 1 | 0 | 1 |
| Nasal Secretions | 11 | 0 | 11 |
| Tissue Block | 6 | 1 | 7 |
| Urine | 18 | 4 | 22 |
| Other | 3 | 0 | 3 |
| Total: | 39 | 5 | 44 |

EXAMPLE 6

Detection Tricothecenes in Body Fluids and Tissues

This assay provides a procedure for the quantitative detection of Trichothecenes including Roridin A, E, H and L-2, Satratoxin G and H, Isosatratoxin F, Verrucarin A and J, and Verrucarol in human tissue and human body fluids treated as described in Examples 2 and 3.

Tricothecenes were measured using a kit provided by Envirologic Inc, (ENVIROLOGIX QuantiTox Kit (EP-100) for Trichothecenes; Envirologic, Inc. Portland, Me.). The Envirologic kit is based on a competitive Enzyme-Linked Immunosorbent Assay (ELISA). In the test, Trichothecenes in a sample compete with enzyme (horseradish peroxidase)-labeled satratoxin for a limited number of antibody binding sites on the surface of the test wells. After a simple wash step, the outcome of the competition is visualized using a color development step. As with all competitive immunoassays, sample concentration is inversely proportional to color development (i.e., darker color=lower concentration of Trichothecenes in the sample and lighter color=higher concentration of Trichothecenes in the sample).

All plate kit components were stored at 4-8° C. when not in use. The kit components were never exposed to temperatures greater than 37° C. or less than 2° C. All reagents were allowed to reach ambient temperature before use. Reagents or test well strips from one plate kit were not used with reagents or test well strips from a different plate kit. Substrate was not exposed to sunlight during pipetting or while incubating samples in the test wells.

PBS Extraction/Dilution Buffer was prepared by making 1.0 liter of PBS, pH 7.4±0.05 in deionized water. PBS was stored refrigerated when not being used to prevent bacterial contamination. PBS was warmed to room temperature prior to use. Roridin A calibrators in PBS Extraction/Dilution Buffer were made daily in PBS using a positive-displacement pipet. At the end of the day, any unused calibrators were disposed of by adding to a 10% bleach solution. The calibrators were as follows:

18.0 ppb Roridin A calibrator=20 μl of 900 ppb stock solution into 980 μl PBS in a glass tube.

2.0 ppb Roridin A calibrator=100 μl of 18 ppb calibrator into 800 μl PBS in a glass tube.

0.2 ppb Roridin A calibrator=10 μl of 18 ppb calibrator in 890 μl PBS in a glass tube.

Negative Calibrator: use an aliquot of the PBS stock.

Once all of the components had reached room temperature, the plate was removed from the pouch. All calibrators, sample extracts, and pipettes were organized so that the samples and enzyme conjugates could be added to the wells in 10 minutes or less. Fifty 50 μl of negative calibrator (NC), 50 μl of each Roridin A calibrator (C1-C3) and 50 μl of each sample extract (S1-S8) were added rapidly to their respective wells. Fifty μl of Enzyme Conjugate (Satratoxin Enzyme Conjugate), was rapidly added to each well.

The contents of the wells were mixed thoroughly by moving the plate frame in a rapid circular motion on the bench top for 30-45 seconds. The wells were covered with tape or parafilm and incubated at ambient temperature for 45 minutes with or without shaking on an orbital shaker at 200 rpm. After incubation, the covering was removed and the contents of the wells removed into a suitable container. The wells were flooded with water and then shaken to empty the wells a total of five times. The plate was then inverted several times on a paper towel to remove as much water as possible.

A 100 μl aliquot of substrate was then added to each well and the contents thoroughly mixed as described in the preceding paragraph. The wells were covered with new tape or parafilm and incubated for 15 minutes at ambient temperature with or without an orbital shaker. To stop the color development reaction, 100 μl of 1.0 N hydrochloric acid was added to each well and the samples were mixed thoroughly. This turned the well contents yellow. The plate was read within 30 minutes of the addition of the HCl using a Multiskan MCC 341 Microplate Reader at a wavelength of 450 nm.

New kit lots were tested in parallel with the kit lots currently in use. In order to test the new lot, one sample from the test batch was processed twice in the same protocol using both the new kit lot and the old kit lot. If the results from the new lot differed from the current lot, the lot test was repeated or the reagent was discarded.

A semi-log curve fit for the standard curve was used to plot the points of the calibrators. See below as example in the data reduction worksheet.

| Calib. Conc. | rep1 | rep 2 | Avg. Value | % CV | B/Bo | Log (Conc.) | Conc. | |
|---|---|---|---|---|---|---|---|---|
| Neg. Ctl. Abs. = | 1.208 | 1.201 | 1.205 | 0.4% | | | | $R^2 = -0.9980$ |
| 0.2 ppb Abs. = | 1.023 | 1.084 | 1.054 | 4.1% | 0.87 | −0.70 | 0.20 | Slope = −0.3524 |
| 2.0 ppb Abs. = | 0.657 | 0.671 | 0.664 | 1.5% | 0.55 | 0.30 | 2.00 | Intercept = 0.7950 |
| 18 ppb Abs. = | 0.359 | 0.372 | 0.366 | 2.5% | 0.30 | 1.26 | 18.00 | |

Figure 2:
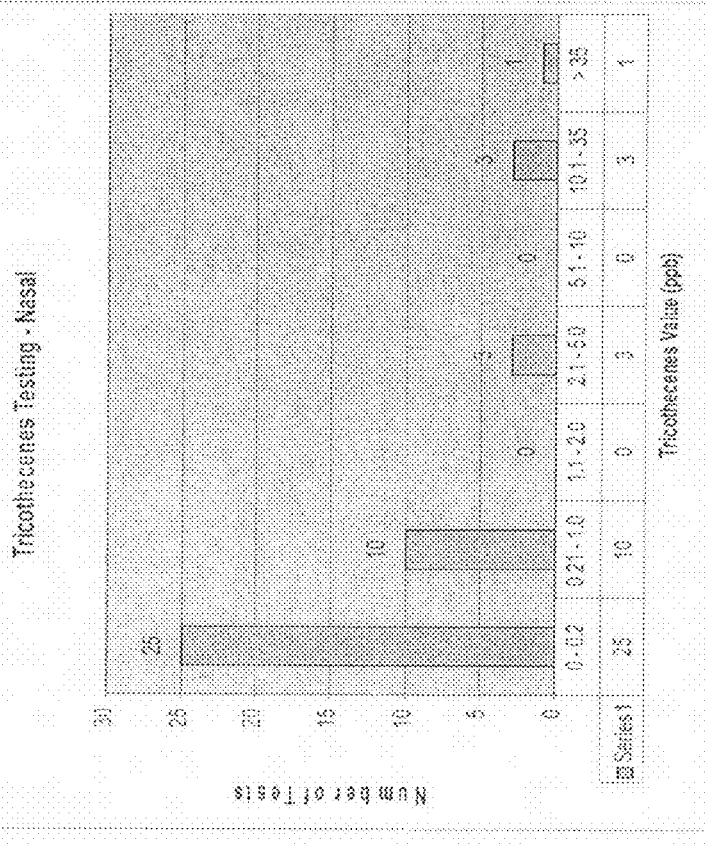
FIG. 2 shows Tricothecenes values for nasal secretions.

Samples were run in duplicate and were plotted to give results in parts per billion (ppb) or nanograms/ml (see FIGS. 1 and 2).

| TRICOTHECENES PANEL | | | |
|---|---|---|---|
| Specimen | 0-0.2 ppb | >0.2 ppb | # of Tests |
| CSF | 0 | 2 | 2 |
| Nasal Secretions | 26 | 16 | 42 |
| Tissue Block | 5 | 8 | 13 |
| Urine | 5 | 104 | 109 |
| Other | 4 | 2 | 6 |
| Total: | 40 | 132 | 172 |

EXAMPLE 7

Detection of Fungal DNA

The target organisms for detection of fungal DNA using a PCR-based approach are shown in the following table. The table also indicates the primer-probe set (number in parentheses in the table) used for amplification and detection. The primers and probes used for amplification and detection of fungal DNA are also shown below.

| Targets: | | | | |
|---|---|---|---|---|
| *Aspergillus* | *Penicillium* | *Stachybotyrous* | *Fusarium* | Control |
| (24) *amstelodami* | (15) *aurantiogriseum* | (1) *chartarum* | (14) *solani* | (6) GEO |
| (7) *flavus* | (4) *chrsogenum* | (23) *echinata* | | |
| (8) *fumigatus* | (16) *citrinum* | | | |
| (9) *nidulans* | (17) *corylophilum* | | | |
| (3) *niger* | (18) *crustosum* | | | |
| (10) *ochraceus* | (20) *fellutanum* | | | |
| (11) *parasiticus* | (21) *roquefortii* | | | |
| (12) *sydowii* | (22) *simplisticum* | | | |
| (13) *ustus* | (5) *verrucosum* | | | |
| (2) *versicolor* | (19) *expansium* | | | |

```
Target 1-S. chartarum
Probe 1 char:     5'-ttgcttcggcgggaacgccccg      (SEQ ID NO: 1)

Primer F2:        5'-gcggagggatcattaccgag         (SEQ ID NO: 2)

Primer R2:        5'-atcgatgccagagccaagag         (SEQ ID NO: 3)

Target 2-A. versicolor
Probe 2 vers:     5'-cggggagccctctcggggc          (SEQ ID NO: 4)

Primer F1:        5'-cgtaggtgaacctgcggaag         (SEQ ID NO: 5)

Primer R1:        5'-atcgatgccggaaccaagag         (SEQ ID NO: 6)

Target 3-A. niger
Probe 3 niger:    5'-tgtctattgtacctgttgcttc       (SEQ ID NO: 7)

Primer F14:       5'-cgtaggtgaacctgcggaag         (SEQ ID NO: 8)

Primer R1:        5'-atcgatgccggaaccaagag         (SEQ ID NO: 9)

Target 4-P. chrysogenum
Probe 4 chry:     5'-ctctgtctgaagattgtagtctgagt   (SEQ ID NO: 10)

Primer F1:        5'-cgtaggtgaacctgcggaag         (SEQ ID NO: 11)

Primer R1:        5'-atcgatgccggaaccaagag         (SEQ ID NO: 12)

Target 5-P. verrucosum
Probe 5 verru:    5'-cccgcctttgctggccgcc          (SEQ ID NO: 13)

Primer F1:        5'-cgtaggtgaacctgcggaag         (SEQ ID NO: 14)

Primer R1:        5'-atcgatgccggaaccaagag         (SEQ ID NO: 15)

Target 6-G. candidum
For Geo F1H:      5'-ggatctcttggttctcgtatc        (SEQ ID NO: 16)

Rev Geo R1H:      5'-cttgatctgaggttgaatagtg       (SEQ ID NO: 17)
```

-continued

```
Probe 6 geo:      5"-aacgcacattgcactttggggtatc   (SEQ ID NO: 18)

Target 7-A. flavus
Probe 7 flav:     5'-cccgccattcatggccgccggg      (SEQ ID NO: 19)

Primer F1:        5'-cgtaggtgaacctgcggaag        (SEQ ID NO: 20)

Primer R1:        5'-atcgatgccggaaccaagag        (SEQ ID NO: 21)

Target 8-A. fumigatus
Probe 8 fumi:     5'-aaagtatgcagtctgagttgattatc  (SEQ ID NO: 22)

Primer F1:        5'-cgtaggtgaacctgcggaag        (SEQ ID NO: 23)

Primer R1:        5'-atcgatgccggaaccaagag        (SEQ ID NO: 24)

Target 9-A. nidulans
Probe 9 nid:      5'-cccaggggcgagccgccgg         (SEQ ID NO: 25)

Primer F1:        5'-cgtaggtgaacctgcggaag        (SEQ ID NO: 26)

Primer R1:        5'-atcgatgccggaaccaagag        (SEQ ID NO: 27)

Target 10-A. ochraceus
Probe 10 ochr:    5'-acaccaacgtgaacactgtctgaag   (SEQ ID NO: 28)

Primer F1:        5'-cgtaggtgaacctgcggaag        (SEQ ID NO: 29)

Primer R1:        5'-atcgatgccggaaccaagag        (SEQ ID NO: 30)

Target 11-A. paraciticus
Probe 11 para:    5'-cgggcccgccgtcatggccg        (SEQ ID NO: 31)

Primer F1:        5'-cgtaggtgaacctgcggaag        (SEQ ID NO: 32)

Primer R1:        5'-atcgatgccggaaccaagag        (SEQ ID NO: 33)

Target 12-A. sydowii
Probe 12 syd:     5'-ccctcggggcgagccgccg         (SEQ ID NO: 34)

Primer F1:        5'-cgtaggtgaacctgcggaag        (SEQ ID NO: 35)

Primer R1:        5'-atcgatgccggaaccaagag        (SEQ ID NO: 36)

Target 13-A. ustus
Probe 13 ust:     5'-ccacaccgaacctcttgttatagc    (SEQ ID NO: 37)

Primer F1:        5'-cgtaggtgaacctgcggaag        (SEQ ID NO: 38)

Primer R1:        5'-atcgatgccggaaccaagag        (SEQ ID NO: 39)

Target 14-F. solani
Probe 14 salani:  5'-cgggaatagacggccccgtgaaac    (SEQ ID NO: 40)

Primer F2:        5'-gcggagggatcattaccgag        (SEQ ID NO: 41)

Primer R2:        5'-atcgatgccagagccaagag        (SEQ ID NO: 42)

Target 15-P. aurantiogriseum
Probe 15 auran:   5'-cccgcctttactggccgccgg       (SEQ ID NO: 43)

Primer F1:        5'-cgtaggtgaacctgcggaag        (SEQ ID NO: 44)

Primer R1:        5'-atcgatgccggaaccaagag        (SEQ ID NO: 45)

Target 16-P. citrinum
Probe 16 citr:    5'-tgttgcctcggcgggccccgc       (SEQ ID NO: 46)

Primer F4:        5'-ggaaggatcattaccgagtg        (SEQ ID NO: 47)

Primer R1:        5'-atcgatgccggaaccaagag        (SEQ ID NO: 48)

Target 17-P. corylophilum
Probe 17 corylo:  5'-ttattgtaccttgttgcttcggcgg   (SEQ ID NO: 49)

Primer F1:        5'-cgtaggtgaacctgcggaag        (SEQ ID NO: 50)

Primer R1:        5'-atcgatgccggaaccaagag        (SEQ ID NO: 51)

Target 18-P. crustosum
```

```
                             -continued
Probe 18 crust:    5'-cgatctccggggacgggcc      (SEQ ID NO: 52)

Primer F7:         5'-ctgtccgagcgtcattgctg     (SEQ ID NO: 53)

Primer R5:         5'-cgaggaccggacgcggtg       (SEQ ID NO: 54)

Target 19-P. expansum
Probe 19 expan:    5'-agacaccccgaactctgcctgaa  (SEQ ID NO: 55)

Primer F1:         5'-cgtaggtgaacctgcggaag     (SEQ ID NO: 56)

Primer R1:         5'-atcgatgccggaaccaagag     (SEQ ID NO: 57)

Target 20-P. fellutanum
Probe 20 fell:     5'-cccgcctgccaggccgccg      (SEQ ID NO: 58)

Primer F1:         5'-cgtaggtgaacctgcggaag     (SEQ ID NO: 59)

Primer R1:         5'-atcgatgccggaaccaagag     (SEQ ID NO: 60)

Target 21-P. roquefortii
Probe 21 roque:    5'-cacccgtgtttatttaccttattgc (SEQ ID NO: 61)

Primer F1:         5'-cgtaggtgaacctgcggaag     (SEQ ID NO: 62)

Primer R1:         5'-atcgatgccggaaccaagag     (SEQ ID NO: 63)

Target 22-P. simplicissimum
Probe 22 simpl:    5'-cacccgtgtttatcgtaccttgttg (SEQ ID NO: 64)

Primer F1:         5'-cgtaggtgaacctgcggaag     (SEQ ID NO: 65)

Primer R1:         5'-atcgatgccggaaccaagag     (SEQ ID NO: 66)

Target 23-S. echinata
Probe 23 echin:    5'-ttgcttcggcgggagagcccg    (SEQ ID NO: 67)

Primer F2:         5'-gcggagggatcattaccgag     (SEQ ID NO: 68)

Primer R2:         5'-atcgatgccagagccaagag     (SEQ ID NO: 69)

Target 24-E. amstelodami
Probe 24 amst:     5'-tgtctatctgtaccctgttgcttcg (SEQ ID NO: 70)

Primer F1:         5'-cgtaggtgaacctgcggaag     (SEQ ID NO: 71)

Primer R1:         5'-atcgatgccggaaccaagag     (SEQ ID NO: 72)

Fungal Universal Group 1
UP1:               5'-cctcggatcaggtagggatac    (SEQ ID NO: 73)

UF1:               5'-atgcctgtccgagcgtcatt     (SEQ ID NO: 74)

UR1:               5'-ttcctccgcttattgatatg     (SEQ ID NO: 75)

Fungal Universal Group 2
Up2:               5'-acggatctcttggctctggcatc  (SEQ ID NO: 76)

F2:                5'-gcggagggatcattaccgag     (SEQ ID NO: 77)

UR2:               5'-ttcactgaattctgcaattcac   (SEQ ID NO: 78)
```

Extraction Methods:

Bead Beater Tube Preparation:
1. 0.3 g±0.01 g of silica bead beating glass (Sigma-Aldrich Cat. no G1277) was added to 2 ml screw cap tube avoiding glass beads in the cap or around the rim.
2. The tubes containing the beads were sterilized in an autoclave on the dry cycle for 10 minutes.
3. The tubes were removed from the autoclave (proceed to the next step).

Solution Preparation:
4. Buffers ATL (from DNAeasy® Tissue Kit, Cat. no. 69506 (Quiagen, Stanford Valencia, Calif.)) and AL (from DNAeasy® Tissue Kit, Cat. no. 69506) may form precipitates upon storage. If a precipitate formed in either buffer, the buffer was incubated at 55° C. until the precipitate fully dissolved.
5. Buffers AW1 and AW2 (from DNAeasy® Tissue Kit, Cat. no. 69506) were supplied as concentrates. Before using for the first time, the appropriate amounts of ethanol (96-100%) were added to Buffers AW1 and AW2 as indicated on the bottles.
6. A 55° C. heat block and a 70° C. heat block were prepared for use in the assay.

Preparation of the Spore Solution or Tissue:
7. If frozen material was used, it was equilibrated to room temperature.
8. About 25.0 mg of paraffin-embedded tissue was weighed or 10.0 µl of spore solution was placed in a 2.0 ml screw cap tube.
9. 180.0 µl of ATL Buffer and 20.0 µl of Proteinase K was added to each sample making sure that the lysate was not gelatinous.

10. 10.0 μl of the Geo Spore reference DNA was added to each sample. (See Assay Specific Procedure for information regarding internal and external controls)
11. All samples were bead beated on the Bead Beater for 1 minute at the speed of 45.
12. Samples were incubated at 55° C. on a pre-warmed heat block for 1 hour.

Extraction of Nucleic Acid:

15. The samples were removed from the heat block and vortexed 15 seconds.
16. 200 μl of Buffer AL was added and incubated at 70° C. for 10 minutes.
17. The tubes were removed from the 70° C. heat block and add 200 μl of ethanol
18. 200 μl of ethanol was added to each tube and vortexed.
19. The mixture underneath the layer of paraffin was pipetted for each sample, making sure not to pipette the silica beads, into the corresponding DNeasy® Mini Spin Column 2 ml collection tube combo for that sample.
20. The columns were centrifuged in a microcentrifuge at 8000 RPM for 1 minute. The collection tube containing the flow through was discarded.
21. Each spin column was placed in a new 2.0 ml collection tube.
22. 500.0 μl of Buffer AW1 was added to each column and centrifuged at 8000 RPM for 1 minute. The collection tube containing the flow through was discarded.
23. Each spin column was placed in a new 2.0 ml collection tube.
24. 500.0 μl of Buffer AW2 was added to each column and centrifuged at 13,000 RPM for 5 minute.
25. The spin columns were removed carefully from the collection tubes so as not to splash nozzles. The collection tube containing the flow through was discarded.
26. The spin columns were placed in their corresponding 1.5 ml elution tube.
27. 100.0 μl of Buffer AE (from DNAeasy® Tissue Kit, Cat. no. 69506) was placed into each spin column and incubated for 3 minutes at room temperature.
28. The spin columns were centrifuged at 8000 RPM for 1 minute. The spin columns were discarded and capped and the extracted nucleic acid samples were stored at −20° C.

Real-Time PCR:
Preparation and Reaction Setup
1. Dilution of Probe Stocks
   a. Resuspend the lyophilized probes in PCR grade water to a final concentration of 100 μM.
      (Example: If the synthesis yields 15.03 nMoles, add 150.3 of PCR grade water to achieve 100 μM concentration)
2. Dilution of Primer Stocks
   a. Resuspend the lyophilized primers in PCR grade water to a final concentration of 100 μM.
      (Example: If the synthesis yields 38.6 nMoles, add 386 μl of PCR grade water to achieve 100 μM concentration)
3. Preparation of Primer/Probe Working Stock
   a. See Appendix A for the working Stock setup for each target.
4. Reaction Setup
   a. The reaction setup for one reaction is shown below. In some cases the addition of $MgCl_2$ or varying concentrations of primer/probe mix is required for PCR. (See Appendix A)

| | |
|---|---|
| DNA | 5.0 μl |
| Primer/Probe Working Stock | 3.5 μl |
| | (Final Concentration see appendix A) |
| OmniMix Beads | 0.5 μl |
| | Beads (no volume contribution) |
| PCR Grade Water | 16.5 μl |
| Total | 25.0 μl |

(Note that during reaction setup a master mix will be prepared for multiple reactions using the Smart Cycler PCR Worksheet (20.4007F). See following sections.)

5. Smart Cycler Cycling Parameters (Omni Fungal I)
   a. Omni Fungal I is the primary program used for the fungal real time assays and the run parameters for this program are outlined below. Cases may occur where changes to this program may be necessary for a specific target or specimen type. See SmartCycler Operation (20.2008S) for further instruction on programming and run optimization utilizing the Smart Cycler software.
   Step 1 (1 Cycle)
   Hot Start: 95° C. for 120 seconds
   Step 2 (45 cycles)
   Denature: 95° C. for 5 seconds
   Anneal: 60° C. for 45 seconds
   See Example PCR Worksheet: (Note: sheet has been truncated to show 3 target sets.)

| | | | | | | |
|---|---|---|---|---|---|---|
| | | II. Master Mix Setup | | | | |
| | Reagent | Lot # | Volume (uL) | Reaction No. | Total Amount | Target |
| Set 1 | | | | | | |
| 1 | H2O | 4532 | 16.5 | 6 | 99.0 | (3) *A niger* |
| 2 | P/P Working Stock | 040505 | 3.5 | 6 | 21.0 | |
| 3 | Omni Mix (Bead) | 2456 | 0.5 | 6 | 3.0 | |
| 4 | MgCl2 | NA | 0.0 | 0 | 0.0 | |
| Set 2 | | | | | | |
| 1 | H2O | 4532 | 16.5 | 6 | 99.0 | (2) *A Versicolor* |
| 2 | P/P Working Stock | 020705 | 3.5 | 6 | 21.0 | |
| 3 | Omni Mix (Bead) | 2456 | 0.5 | 6 | 3.0 | |
| 4 | MgCl2 | NA | 0.0 | 0 | 0.0 | |

-continued

| II. Master Mix Setup | | | | | |
|---|---|---|---|---|---|
| Reagent | Lot # | Volume (uL) | Reaction No. | Total Amount | Target |
| Set 2 | | | | | |
| 1 H2O | 4532 | 16.5 | 4 | 66.0 | (6) Geo |
| 2 P/P Working Stock | 020705 | 3.5 | 4 | 14.0 | |
| 3 Omni Mix (Bead) | 2456 | 0.5 | 4 | 2.0 | |
| 4 MgCl2 | NA | 0.0 | 0 | 0.0 | |

*Add MgCl$_2$ as needed per target subtract volume used from water added to maintain a 20 µl reaction.
Add 20 µl of Master Mix to each tube and then add 5.0 µl of template for a total volume of 25.0 µl.

APPENDIX A

Target Working Stock Recipes

| Target | P1 100 uM | Final Conc. | P2 100 uM | Final Conc. | Probe 100 uM | Final Conc. | MgCl2 1 M | Final Conc. | Water | Final Volume |
|---|---|---|---|---|---|---|---|---|---|---|
| 1 | 15.0 uL | .3 uM | 15.0 uL | .3 uM | 10.0 uL | .2 uM | NA | NA | 660 uL | 700 uL |
| 2 | 30.0 uL | .6 uM | 30.0 uL | .6 uM | 20.0 uL | .4 uM | NA | NA | 620 uL | 700 uL |
| 3 | 30.0 uL | .6 uM | 30.0 uL | .6 uM | 20.0 uL | .4 uM | 30.0 uL | 6 mM | 590 uL | 700 uL |
| 4 | 15.0 uL | .3 uM | 15.0 uL | .3 uM | 10.0 uL | .2 uM | NA | NA | 660 uL | 700 uL |
| 5 | 15.0 uL | .3 uM | 15.0 uL | .3 uM | 10.0 uL | .2 uM | NA | NA | 660 uL | 700 uL |
| 6 | 15.0 uL | .3 uM | 15.0 uL | .3 uM | 10.0 uL | .2 uM | NA | NA | 660 uL | 700 uL |
| 7 | 15.0 uL | .3 uM | 15.0 uL | .3 uM | 10.0 uL | .2 uM | NA | NA | 660 uL | 700 uL |
| 8 | 15.0 uL | .3 uM | 15.0 uL | .3 uM | 10.0 uL | .2 uM | 20.0 | 4 mM | 640 uL | 700 uL |
| 9 | 15.0 uL | .3 uM | 15.0 uL | .3 uM | 10.0 uL | .2 uM | NA | NA | 660 uL | 700 uL |
| 10 | 15.0 uL | .3 uM | 15.0 uL | .3 uM | 10.0 uL | .2 uM | NA | NA | 660 uL | 700 uL |
| 11 | 15.0 uL | .3 uM | 15.0 uL | .3 uM | 10.0 uL | .2 uM | 20.0 | 4 mM | 640 uL | 700 uL |
| 12 | 15.0 uL | .3 uM | 15.0 uL | .3 uM | 10.0 uL | .2 uM | NA | NA | 660 uL | 700 uL |
| 13 | 30.0 uL | .6 uM | 30.0 uL | .6 uM | 20.0 uL | .4 uM | NA | NA | 620 uL | 700 uL |
| 14 | 45.0 uL | .9 uM | 45.0 uL | .9 uM | 30.0 uL | .6 uM | NA | NA | 580 uL | 700 uL |
| 15 | 15.0 uL | .3 uM | 15.0 uL | .3 uM | 10.0 uL | .2 uM | NA | NA | 660 uL | 700 uL |
| 16 | 15.0 uL | .3 uM | 15.0 uL | .3 uM | 10.0 uL | .2 uM | NA | NA | 660 uL | 700 uL |
| 17 | 15.0 uL | .3 uM | 15.0 uL | .3 uM | 10.0 uL | .2 uM | NA | NA | 660 uL | 700 uL |
| 18 | 30.0 uL | .6 uM | 30.0 uL | .6 uM | 20.0 uL | .4 uM | 20.0 ul | 4 mM | 600 uL | 700 uL |
| 19 | 15.0 uL | .3 uM | 15.0 uL | .3 uM | 10.0 uL | .2 uM | 20.0 | 4 mM | 640 uL | 700 uL |
| 20 | 15.0 uL | .3 uM | 15.0 uL | .3 uM | 10.0 uL | .2 uM | NA | NA | 660 uL | 700 uL |
| 21 | 15.0 uL | .3 uM | 15.0 uL | .3 uM | 10.0 uL | .2 uM | NA | NA | 660 uL | 700 uL |
| 22 | 15.0 uL | .3 uM | 15.0 uL | .3 uM | 10.0 uL | .2 uM | 20.0 | 4 mM | 640 uL | 700 uL |
| 23 | 15.0 uL | .3 uM | 15.0 uL | .3 uM | 10.0 uL | .2 uM | NA | NA | 660 uL | 700 uL |
| 24 | 15.0 uL | .3 uM | 15.0 uL | .3 uM | 10.0 uL | .2 uM | NA | NA | 660 uL | 700 uL |

Mix target working stocks for each target as described in the table above by combining the amounts noted for Primer 1, Primer 2, Probe, MgCl$_2$ (if needed), and water. Use 3.5 µl of this working stock for each reaction performed.

Master Mix Preparation:
1. All steps were performed under sterile conditions.
2. After the water and beads had been pipetted into to the individual tubes, the tubes were mixed until the beads (Cat no. Omni 1-100N-050; Cepheid, Sunnyvale, Calif.) were completely dissolved.
3. After the beads were dissolved, the appropriate primer/probe working stock was pipetted into each master mix tube as described in the PCR worksheet.
4. The solutions were mixed completely and the working stocks returned to the −20° C. freezer.
5. Controls—
   a. Internal Control—Every clinical sample processed was inoculated with spores from the internal control target Geometrica to show that a negative target result is a true negative result and not related to the extraction of the sample. The samples were processed through the extraction protocol and amplified and detected utilizing primer and probes specific for Geometrica.
   b. Positive Control—A positive control for each target of interest (Primer/Probe sets) was processed along with each clinical sample in each real-time PCR run. This positive control can be extracted from tissue or spore solutions but must be lot checked prior to use. The positive control shows that the primer/probe set for each target is not being inhibited and shows that a negative result is a true negative.
   c. Negative Control—A negative control for each target of interest (Primer/Probe sets) was processed along with each clinical sample in each real-time PCR run. This negative control can be extracted from tissue or water but must be lot checked prior to use. The negative control shows that the primer/probe set, water and extraction reagents for each target is not contaminated with the target and shows that a positive result is a true positive.

Addition of Target Nucleic acid:
1. 5.0 µl of the negative control, positive control and patient samples was pipetted into the appropriate reaction tubes.
2. The reaction tubes were centrifuged using the Smart Cycler® II modified centrifuge.
3. The tubes were returned to the cooling block and stored at 4° C. or the Smart Cycler Setup and Run was conducted.

Smart Cycler Setup and Run:
1. The Omni Fungal I protocol or the appropriate protocol was selected for this real-time run.

2. For information regarding the operation of the Smart Cycler see SmartCycler Operation (20.2008S) (Smart Cycler® II Instrument; Cepheid, Sunnyvale, Calif.).

Data Analysis:
1. After the run is completed the results were analyzed by reviewing each site in the results table. If a specific sample tested was registered as positive by the software there was a positive in the results column for that sample. There was also a crossing point registered in the Ct column for that sample.
2. After reviewing the Results Table, the curves were reviewed for each sample by selecting the "FAM" or "Log FAM" of the "Views" menu.
3. With the graph selected, all samples that created a curve were present on the screen. Each sample was reviewed independently by clicking on the Site ID associated with the sample of interest located just to the right of the graph.
4. A sample was analyzed as positive by the software if the curve broke the baseline of 30 (default set in section above) before the end of the 45 cycles and negative if it did not break the baseline of 30 before the end of the 45 cycles.
5. Each sample was reviewed and then highlighted so that all sample curves were present on the graph.

Results Interpretation:
1. Positive Result: A positive result is defined as any amplification observed crossing a baseline fluorescence of ≥30 between cycles 1 and 40 of the real-time PCR run.
2. Negative Result: A negative result is defined as no amplification observed crossing a baseline fluorescence of ≥30 between cycles 1 and 40 of the PCR run.
3. Equivocal Result: An equivocal result is defined as no amplification observed crossing a baseline fluorescence of ≥30 between cycles 1 and 40, a control out of range or questions regarding sample integrity.
4. Positive Control: A control that is positive for the target being tested and shows that the assay will show a positive in the presence of target spores and that there is not PCR inhibition.
5. Negative Control: A control that is negative for the target being tested and shows that the reagents or the sample were not contaminated with the target prior to the testing of the sample.
6. Internal Control: A control used to show that the extraction process is working fine for the purification of nucleic acid from the clinical specimen and that a negative result is truly negative and not due to an issue associated with the extraction. (Note: the internal control must be positive for any sample to be reported as negative for a target.)

See Table Below:

|  | Crossing Point | Positive Control | Negative Control | Internal Control |
|---|---|---|---|---|
| Reportable Result |  |  |  |  |
| Positive Result | ≥40 | (+) | (−) | (+) |
| Positive Result | ≥40 | (−) | (−) | (+) |
| Positive Result | ≥40 | (+) | (−) | (−) |
| Positive Result | ≥40 | (−) | (−) | (−) |
| Negative Result | (−) | (+) | (−) | (+) |
| Negative Result | (−) | (+) | (+) | (+) |
| Negative Result | (−) | (−) | (+) | (+) |
| Un-reportable Result |  |  |  |  |
| Positive Result | ≥40 | (+) | (+) | (+) |
| Positive Result | ≥40 | (−) | (+) | (+) |
| Positive Result | ≥40 | (+) | (+) | (−) |
| Positive Result | ≥40 | (−) | (+) | (−) |
| Negative Result | (−) | (−) | (−) | (+) |
| Negative Result | (−) | (+) | (−) | (−) |
| Negative Result | (−) | (+) | (+) | (−) |
| Equivocal Result |  |  |  |  |
| Case by Case | Case by Case | Case by Case | Case by Case | Case by Case |

In other illustrative embodiments, results can be determined based on a cycle range between cycles 1 and 45 of the PCR run or other useful ranges can be used.

| | DNA RESULTS- | | |
|---|---|---|---|
| Tissue | Pos Results/ tissue | Neg Results/ tissue | Isolates ** |
| Lung | 6 | 1 | *Aspergillus fellutanum* (1) *Asp. niger* (2) *P. crysogenum* (3) |
| Liver | 5 | 2 | *Asp flavus* (2) *Asp. Niger* (3) *Pen. versicolour* (2) *Asp. Fumigatus* (1) |
| Brain | 4 | 2 | *Asp niger* (2) *Asp fumigatus* (2) *Asp. flavus* (2) |
| Skin | 2 | 1 | *Penicillium fellutanum* (1) *Pen. crysogenum* (1) *Asp. ustus* (1) |
| Respiratory ## | 3 | 6 | *Asp. niger* (2) *Asp. flavus* (2) *Pen. versicolour* (1) |

** some specimens revealed more than one isolate
includes nasal secretions, inner ear fluids, and sputums The test is 100% specific for the isolates tested for.
15 known negative (non-exposed) patients were tested in validation. No positive results with the probes in this patent were found.
Of the 29 suspected exposed patients tested, 29 samples of tissue were tested. Of those 29 tissues/fluids, 20 specimens gave results of one or more organisms by DNA probing using RT-PCR.

EXAMPLE 8

Detection of Fungal DNA Using Universal Primers

The purpose of the universal fungal assays is to check clinical samples for the presence of fungal DNA prior to running multiple fungal target specific assays. Two universal assays were designed for this purpose. Fungal assay UP1 was designed to detect the presence of fungal *Aspergillus* and *Penicillium* species. Fungal assay UP2 was designed to detect the presence of *Stachybotrys* and *Fusarium* species. Each assay is composed of two primers and one Taqman probe specific for fungal targets of the species described above.

To identify sequence present in 1.) all *Aspergillus* and *Penicillium* species, and in 2.) all *Stachybotrys* and *Fusarium* species a search was performed for public sequence and sequence was identified. A sequencing primer (oligonucleotide ~20 bases long) was designed specific for each of the targets of interest, and was ordered from a vender. The primers and target DNAs were sequenced, and the accuracy confirmed. Primers and probes were designed and were expected to be specific for all individual targets in each species group as described below. To check for specificity to the species groups described, the sequences of each assay were put through a "Blast" search against known sequences from fungal genomes. Initial results showed these sequences to be specific for the species as described above and not specific for clinically relevant targets outside the species.

The following sequences were found to be homologous for all targets of interest related to *Aspergillus* and *Penicillium*:

```
Assay UP1

UF1 atgcctgtccgagcgtcatt   (Forward Primer)   (SEQ ID NO: 74)

UR1 ttcctccgcttattgatatg   (Reverse Primer)   (SEQ ID NO: 75)

UP1 cctcggatcaggtagggatac  (Taqman probe)     (SEQ ID NO: 73)
```

The following sequences were found to be homologous for all targets of interest related to *Stachybotrys* and *Fusarium*:

```
Assay UP2

F2  gcggagggatcattaccgag   (Forward Primer)   (SEQ ID NO: 77)

UR2 ttcactgaattctgcaattcac (Reverse Primer)   (SEQ ID NO: 78)

Up2 acggatctcttggctctggcatc (Taqman probe)    (SEQ ID NO: 76)
```

EXAMPLE 9

Detection of Mycotoxins Using Luminex®

The purpose of this assay is to utilize the Luminex® platform to detect approximately 3 toxin groups (tricothecenes, aflatoxins, and ochratoxins) in patient samples that have been exposed to fungal targets belonging to *Aspergillus, Penicillium, Stachybotrys,* and *Fusarium* species. The Luminex® assay utilizes microspheres (beads) that are coupled to antigens to detect antibodies against those specific antigens in a sample. Samples and coupled microspheres will be incubated in microtitration filter wells where antigen-antibody binding occurs. After incubation and washing, the appropriate detection antibody (e.g., biotinylated antibody) will be introduced and incubated during which antibody-antibody binding occurs. After incubation and washing, a reporter conjugate will be added and incubated where the biotin-binding reaction occurs.

In theory, each microsphere is color-coded into 100 different sets. Each bead set can be coated with a reagent to capture and detect a specific analyte from a sample. The Luminex® 100 has lasers that excite the internal dyes that identify the microsphere and any reporter dye captured during the assay. During the run on the Luminex®, several readings will be made on each of the bead sets. Potentially, this will create a multiplexing capability of up to 100 unique assays with one single sample.

EXAMPLE 10

Detection of Fungal DNA and Mycotoxins in Human Patients

Findings for Patient #1 (Skin Biopsy)
Positive for *P. chrysogenum* and *A. ustrus*
Positive for Trichothecenes (38 ppb)
Findings for Patient #2 (Endometriosis DX in Ovary and Uterus)
Positive for Trichothecenes (25 ppb in ovary pathology specimen)
Findings for Patient #3 (Autopsy Specimen)
Positive for *A. fellutanum* (lung)
Positive for *A. flavus* and *A. niger* (liver)
Positive for *A. niger* (brain)

Findings for Patient #4 (Questionable Fungal Mass on Neck)
Positive for *A. niger* (left and right inner ear)

Positive (left ear) for aflatoxin (9.5 ppb), ochratoxin (4.5 ppb), and Trichothecenes (0.62 ppb)
Positive (right ear) for aflatoxin (0.73 ppb) and Trichothecenes (0.62 ppb)
Findings for Patient #5 (Pilocystic Astrocytoma, Brain Tumor)
6 year old female, Grade 1-2 Pilocystic astrocytoma, Brain
RT-PCR: Negative for 23 probes
Mycotoxins: aflatoxins (3.0 ppb), all other mycotoxins negative.
Findings for Patient #6 (Diagnosis: Pulmonary Fibrosis, Potential Lung Transplant Patient).
38 year old male on oxygen. Previous lung biopsy: severe Interstitial fibrosis (UIP).
All bacterial and fungal cultures negative.
RT-PCR: negative for 23 probes.
Mycotoxins: aflatoxin (4 ppb), all other mycotoxin negative
Treated with antifungal agent, and, after six weeks, he improved and was taken off lung transplant emergent list. Oxygen use decreased significantly.

Findings for Patient #7: (Headache and Seizures)
32 year old female with severe headaches and seizures. All diagnostic tests negative. All cultures negative.
RT-PCR: positive for *Stachybotrys chartarum*.
Findings for Patient #8 (Mouth Lesions for Two Years, No Resolution)
84 year old female with three mouth lesions, chief complaint: pain and mouth feels like "cotton".
Biopsy: parakeratosis, ulceration, no malignant cells, chronic inflammation, increased vascularity. Diagnosis: consistent with history of aphthous stomatitis.
RT-PCR: Positive for *Aspergillus sydowii*.
Findings for Patient #9 (Chronic Headaches)
40 year old male with chronic headaches
Pathology biopsy: Temporal dura and lobe: Perivascular inflammatory cell infiltrate. No neoplasm identified. No organisms noted by stain or culture or PCR for virus or bacteria.
RT-PCR: positive for *Aspergillus ustus* and *Emericella amstelodami*.
Mycotoxins: Negative
Findings for Patient #10 (Patient with Skin Lesions)
56 year old male exposed to *Stachybotrys, Aspergillus niger,* and *Penicillium* sp. (confirmed by Environmental evaluation).
RT-PCR: Skin Biopsy: Positive for *Stachybotrys chartarum, Aspergillus niger*
Mycotoxins: Positive for Aflatoxin (4 ppb); Negative for trichothecenes.

EXAMPLE 11

Detection of Mycotoxins

The purpose of this assay is to utilize the Luminex® platform to detect approximately 29 toxins in patient samples which include but are not limited to blood, spinal fluid, urine, nasal secretions, sputum, and tissue that have been exposed to fungal targets belonging to *Aspergillus, Penicillium, Stachybotrys,* and *Fusarium* species.

The Luminex® assay can, for example, utilize microspheres (beads) that are coupled to monoclonal antibodies to detect mycotoxin antigens. The monoclonal antibodies will be made or purchased for use in this procedure. The antigens are, for example, aflatoxin B1, B2, G1, and G2, Ochratoxin A, and a group of Trichothecenes. The group of Trichothecenes includes Roridin A, E, H and L-2, Satratoxin G and H, Isosatratoxin F, Verrucarin A and J, and Verrucarol, and T-2. Samples and coupled microspheres will be incubated in microtitration filter wells where antigen-antibody binding occurs. After incubation and washing, the appropriate detection antibody (e.g., biotinylated antibody) will be introduced and incubated during which antigen-antibody binding occurs. After incubation and washing, a reporter conjugate will be added and incubated where the biotin-binding reaction occurs.

Each microsphere is color-coded into, for example, 100 different sets. Each bead set can be coated with a reagent to capture and detect a specific analyte from a sample. The Luminex® 100 has lasers that excite the internal dyes that identify the microsphere and any reporter dye captured during the assay. During the run on the Luminex®, several readings will be made on each of the bead sets. Potentially, this assays will create a multiplexing capability of up to 100 unique assays with a single sample.

EXAMPLE 12

Luminex Assay Using DNA Probes Bound to Beads

Microspheres (Luminex Corporation, Austin, Tex.) are 5.6 µm in diameter and are comprised of polystyrene, divinyl benzene, and methacrylic acid with surface carboxylate functionality for covalent attachment of biomolecules. The microspheres are internally dyed with red, infrared-emitting fluorochromes. Spectral addresses were created by adjusting the concentrations of each fluorochrome with each bead set. When the microsphere sets were analyzed with the Luminex 100 instrument (Luminex), each bead set was identified and classified by a distinct fluorescence signature pattern.

Figure 3:
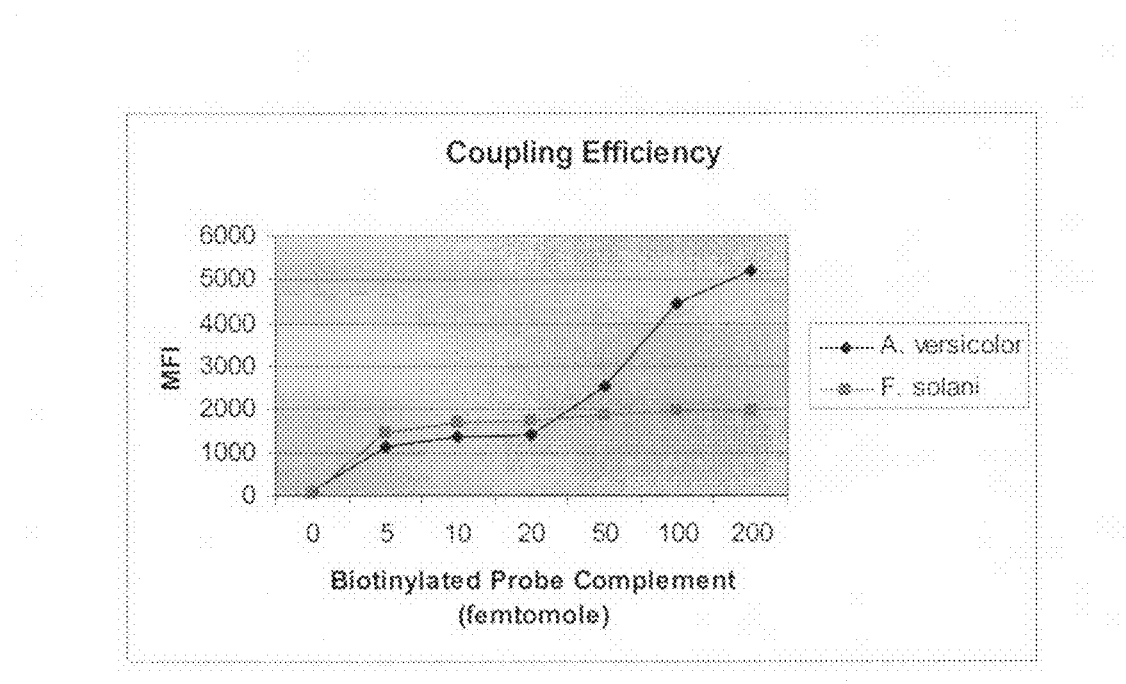
FIG. 3 shows fungal DNA coupling efficiency to microspheres.

Coupling: Two microsphere sets were used for covalent coupling of *A. versicolor* and *mF. solani* probes to carboxyl functional groups on the microsphere surfaces. A concentration of $5.0 \times 10^6$ microspheres were added to separate 1.5 ml microcentrifuge tubes and pelleted by microcentrifugation and the supernatant was aspirated. The microsphere pellet was resuspended and vortexed in 50 µl of 0.1M 2-(N-morpholino)-ethanesulfonic acid (MES), pH 4.5, 0.2 nanomole of each 5' amino-modified capture oligonucleotide or probe (*A. versicolor:* 5'-CGGGGAGCCCTCTCGGGGGC-3' (SEQ ID NO: 4) and *F. solani:* 5'-CGGGAATAGACGGCCCCGT-GAAAC-3' (SEQ ID NO: 40)) and 25 µg of 1-ethyl-3-(3-dimethylaminopropyl)-carbodiimide hydrochloride (EDC) (10 mg/ml in $dH_2O$), and the mixture was incubated for 30 minutes at room temperature in the dark. The microsphere mixture was vortexed and 25 µg of EDC was added again and mixed, and the mixture was incubated for 30 min at room temperature in the dark. One milliliter of 0.02% Tween-20 (0.02% in $dH_2O$) was added to the coupled microspheres and microcentrifuged. The supernatant was removed and the pellet was resuspended in 100 µl of 1× Tris EDTA, pH 8.0 (TE) (diluted in $dH_2O$), by vortex and sonication (see FIG. 3).

Assay: A working mixture of the microspheres was prepared at a concentration of 150 microspheres per microliter in 1.5× TMAC (5M TMAC, 20% Sarkosyl, 1M Tris-HCL, 0.5M EDTA, $H_2O$), vortexed and sonicated. Thirty-three microliters of each microsphere mixture was added to the wells of a 96-well V-bottom PCR plate and 17 µl TE, pH 8.0, were added to the background wells. To each appropriate well 5' biotinylated complementary oligonucleotides (*A. versicolor:* 5'-GCCCCCGAGAGGGCTCCCCG-3' (SEQ ID NO: 90) and *F. solani:* 5'-GTTTCACGGGGCCGTCTATTCCCG-3' (SEQ ID NO: 91)) (5 to 200 femtomoles) and TE, pH 8.0, to a total well volume of 50 µl were added. The reaction wells were mixed, covered and incubated at 96° C. for 3 min to denature any secondary structure. The reactions were incubated for 15 min at 52° C. and 25 µl of a 10 µg/ml dilution of streptavidin-R-phycoerythrin in 1× TMAC (1.5× TMAC diluted in $dH_2O$) was added, mixed and incubated for 5 min at 52° C. Fifty microliters from each well was analyzed at 52° C. with a minimum bead count set at 100 events.

| DataType: Averaged Median | | |
|---|---|---|
| Sample (fmol) | A. versicolor | Total Events |
| 0 | 96 | 215 |
| 5 | 1143 | 213 |
| 10 | 1344 | 215 |
| 20 | 1420 | 223 |
| 50 | 2513 | 205 |

-continued

| DataType: Averaged Median | | |
|---|---|---|
| Sample (fmol) | A. versicolor | Total Events |
| 100 | 4467 | 224 |
| 200 | 5206 | 202 |

| DataType: Averaged Median | | |
|---|---|---|
| Sample (fmol) | F. solani | Total Events |
| 0 | 66 | 224 |
| 5 | 1470 | 213 |
| 10 | 1682 | 215 |
| 20 | 1740 | 205 |
| 50 | 1884 | 221 |
| 100 | 1974 | 210 |
| 200 | 1978 | 223 | copied from output
DataType: Median

| Location | Sample | A. versicolor | Total Events |
|---|---|---|---|
| 1 | 0 | 73 | 220 |
| 2 | 5 | 1358 | 221 |
| 3 | 10 | 1461 | 227 |
| 4 | 20 | 1639 | 230 |
| 5 | 50 | 2512 | 201 |
| 6 | 100 | 3886 | 229 |
| 7 | 200 | 5279 | 201 |
| 8 | 0 | 56 | 200 |
| 9 | 0 | 118 | 209 |
| 10 | 5 | 928 | 205 |
| 11 | 10 | 1227 | 202 |
| 12 | 20 | 1201 | 215 |
| 13 | 50 | 2514 | 209 |
| 14 | 100 | 5047 | 218 |
| 15 | 200 | 5133 | 203 |
| 16 | 0 | 104 | 226 |

| DataType: Median | | | |
|---|---|---|---|
| Location | Sample | F. solani | Total Events |
| 17 | 0 | 99 | 210 |
| 18 | 5 | 1582 | 214 |
| 19 | 10 | 1636 | 204 |
| 20 | 20 | 1800 | 200 |
| 21 | 50 | 1887 | 225 |
| 22 | 100 | 1932 | 212 |
| 23 | 200 | 1960 | 219 |
| 24 | 0 | 136 | 223 |
| 25 | 0 | 32 | 237 |
| 26 | 5 | 1359 | 211 |
| 27 | 10 | 1728 | 226 |
| 28 | 20 | 1681 | 210 |
| 29 | 50 | 1882 | 216 |
| 30 | 100 | 2017 | 207 |
| 31 | 200 | 1997 | 227 |
| 32 | 0 | 94 | 204 |

DNA Coupling Raw Data
SN LX10001089024
Session Operator 022107couplingconfirmarion.RTL
Samples 32 Min Events 0
Results
DataType: Median

| Location | Sample | Aver | Fsol | Total Events | Notes |
|---|---|---|---|---|---|
| 1 | 0 | 73 | | 220 | |
| 2 | 5 | 1358 | | 221 | |
| 3 | 10 | 1461 | | 227 | |
| 4 | 20 | 1639 | | 230 | |
| 5 | 50 | 2512 | | 201 | |
| 6 | 100 | 3886 | | 229 | |
| 7 | 200 | 5279 | | 201 | |
| 8 | 0 | 56 | | 200 | |
| 9 | 0 | 118 | | 209 | |
| 10 | 5 | 928 | | 205 | |
| 11 | 10 | 1227 | | 202 | |
| 12 | 20 | 1201 | | 215 | |
| 13 | 50 | 2514 | | 209 | |
| 14 | 100 | 5047 | | 218 | |
| 15 | 200 | 5133 | | 203 | |
| 16 | 0 | 104 | | 226 | |
| 17 | 0 | | 99 | 210 | |
| 18 | 5 | | 1582 | 214 | |
| 19 | 10 | | 1636 | 204 | |
| 20 | 20 | | 1800 | 200 | |
| 21 | 50 | | 1887 | 225 | |
| 22 | 100 | | 1932 | 212 | |
| 23 | 200 | | 1960 | 219 | |
| 24 | 0 | | 136 | 223 | |
| 25 | 0 | | 32 | 237 | |
| 26 | 5 | | 1359 | 211 | |
| 27 | 10 | | 1728 | 226 | |
| 28 | 20 | | 1681 | 210 | |
| 29 | 50 | | 1882 | 216 | |
| 30 | 100 | | 2017 | 207 | |
| 31 | 200 | | 1997 | 227 | |
| 32 | 0 | | 94 | 204 | |

| DataType: Count | | | | |
|---|---|---|---|---|
| Location | Sample | Aver | Fsol | Total Events |
| 1 | 0 | 100 | 120 | 220 |
| 2 | 5 | 121 | 100 | 221 |
| 3 | 10 | 100 | 127 | 227 |
| 4 | 20 | 130 | 100 | 230 |
| 5 | 50 | 100 | 101 | 201 |
| 6 | 100 | 129 | 100 | 229 |
| 7 | 200 | 100 | 101 | 201 |
| 8 | 0 | 100 | 100 | 200 |
| 9 | 0 | 109 | 100 | 209 |
| 10 | 5 | 105 | 100 | 205 |
| 11 | 10 | 102 | 100 | 202 |
| 12 | 20 | 115 | 100 | 215 |
| 13 | 50 | 109 | 100 | 209 |
| 14 | 100 | 118 | 100 | 218 |
| 15 | 200 | 103 | 100 | 203 |
| 16 | 0 | 100 | 126 | 226 |
| 17 | 0 | 110 | 100 | 210 |
| 18 | 5 | 114 | 100 | 214 |
| 19 | 10 | 104 | 100 | 204 |
| 20 | 20 | 100 | 100 | 200 |
| 21 | 50 | 125 | 100 | 225 |
| 22 | 100 | 112 | 100 | 212 |
| 23 | 200 | 119 | 100 | 219 |
| 24 | 0 | 100 | 123 | 223 |
| 25 | 0 | 100 | 137 | 237 |
| 26 | 5 | 100 | 111 | 211 |
| 27 | 10 | 126 | 100 | 226 |
| 28 | 20 | 100 | 110 | 210 |
| 29 | 50 | 116 | 100 | 216 |

-continued

DataType: Count

| Location | Sample | Aver | Fsol | Total Events |
|---|---|---|---|---|
| 30 | 100 | 100 | 107 | 207 |
| 31 | 200 | 100 | 127 | 227 |
| 32 | 0 | 104 | 100 | 204 |

The data indicate that DNA probes can be bound to beads and can be used to detect the presence of fungal DNA in samples.

EXAMPLE 13

Luminex Indirect Assay Using Antigen Bound to Beads

Microspheres (Luminex Corporation, Austin, Tex.) are 5.6 µm in diameter and are comprised of polystyrene, divinyl benzene, and methacrylic acid with surface carboxylate functionality for covalent attachment of biomolecules. The microspheres are internally dyed with red, infrared-emitting fluorochromes. Spectral addresses were created by adjusting the concentrations each fluorochrome with each bead set. When the microsphere sets were analyzed with the Luminex 100 instrument (Luminex®), each bead set was identified and classified by a distinct fluorescence signature pattern.

Figure 4:
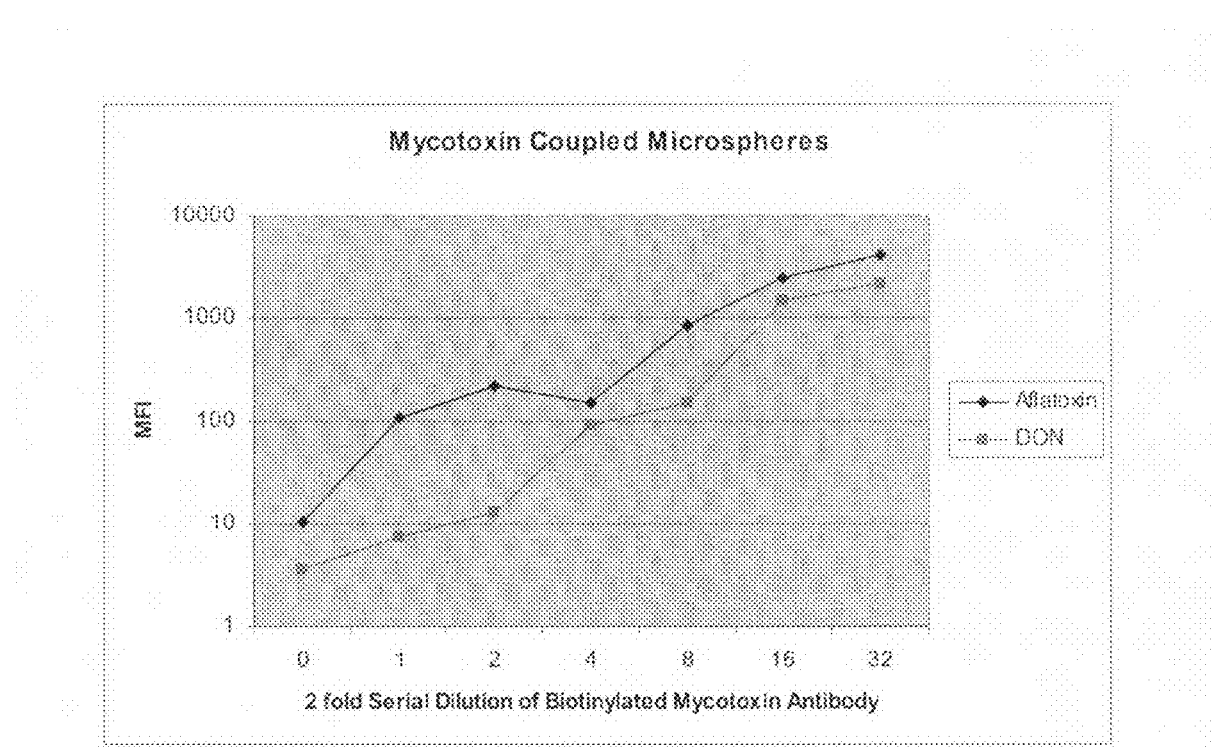
FIG. 4 shows mycotoxin coupling efficiency to microspheres.

Coupling: Two microsphere sets were used for covalent coupling of mycotoxin antigens. Aflatoxin (B1, B2, G1, G2) and Deoxynivalenol (DON) were used and required chemical modifications of carboxyl functional groups on the microsphere surfaces to amine groups due to the absence of an alpha-amino N-terminal group on either antigen. Adipic acid dihydrazide (ADH) was used to modify the carboxyl functional groups on the microsphere surfaces to provide an NH2 group for coupling to each antigen. A concentration of 1.25× $10^7$ microspheres were added to separate 1.5 ml microcentrifuge tubes and were washed by adding 500 µl of 100 mM 2-(N-morpholino)-ethanesulfonic acid (MES), pH 6.0, microcentrifuged at 10,000× g for 1 min at room temperature and the supernatant was aspirated. The microsphere pellet was resuspended and vortexed in 1 ml of ADH and 200 µl of 1-ethyl-3-(3-dimethylaminopropyl)-carbodiimide hydrochloride (EDC) (200 mg/ml in 100 mM MES, pH 6.0) and the tubes were rotated for 1 h at room temperature in the dark. The microspheres were then washed twice with 1 ml of 100 mM MES, pH 4.5, by microcentrifugation as described above, and the supernatants were discarded. Five hundred microliters of each antigen (500 ppb Aflatoxin and 125 ppb DON) were added to each pellet of ADH-modified microspheres and the mixture was incubated at room temperature for 4 h with rotation. To remove any noncovalently bound mycotoxin, the microspheres were washed twice by centrifugation with PBS-Tween and were blocked with PBS-Tween (see FIG. 4).

Immunoassay: In order to test the coupling efficiency of each antigen, Aflatoxin (B1, B2, G1, G2) and Deoxynivalenol (DON), to each microsphere set, an indirect immunoassay must be performed. For the competitive assay, each mycotoxin antibody will be titrated in a two-fold dilution and incubated in micotiter wells of a 96-well plate containing mycotoxin antigen-coupled microspheres. The MFI signal should increase as the antibody is diluted to reach optimal antibody dilution required for the competitive immunoassay. Two blanks will be identified with a "0" which indicates the absence of mycotoxin antibody and a signal of less than 50 MFI (Median Fluroscent Signal). The increasing signal indicating the labeled mycotoxin antibody binding to the antigen-coupled microspheres and the low signal in the blank wells, where no labeled mycotoxin antibody is present, prove that the mycotoxin antigens were effectively coupled to the microsphere sets and can be detected by the appropriate mycotoxin antibodies.

Fifty microliters of each microsphere mixture were added to the wells of a 1.2 µm-pore-size filter membrane microtiter plate. Fifty microliters of PBS-1% BSA were added to each background well. Sheep Anti-Aflatoxin and Sheep Anti-DON antibodies were purified by ammonium sulfate precipitation and desalted utilizing desalting spin columns and were labeled with biotin using sulfosuccinimidyl-6-[biotin-amido] hexanoate. Each mycotoxin antibody was diluted in PBS-1% BSA in 2-fold dilutions and 50 µl of each dilution were added to the standard wells. The wells were mixed by pipetting and the samples were incubated, with shaking, at room temperature in the dark for 1 h. The wells were aspirated using a vacuum manifold filtration system and were washed twice with 100 µl of PBS-1% PBS-BSA. The microspheres were resuspended in 50 µl PBS-1% BSA and 50 µl of 4 µg/ml Streptavisdin-R-phycoerythyrin was added to each well, mixed and incubated, with shaking, at room temperature in the dark for 30 min. The wells were washed twice with 100 µl PBS-1% BSA and the samples were resuspended in 100 µl PBS-1% BSA. Seventy-five microliters of each sample were analyzed with a minimum bead count set at 100 events.

Data: Mycotoxin DON and Aflatoxin were each coupled to two sets of Luminex microspheres. Biotinylated Sheep Anti-DON and Sheep Anti-Aflatoxin were titrated in a two-fold dilution to show a dose response.

Aflatoxin
DataType: Median

| Location | Antibody Dose | Aflatoxin | Total Events |
|---|---|---|---|
| 1 | 0 | 10 | 100 |
| 2 | 0 | 11 | 100 |
| 3 | Neat | 106 | 100 |
| 4 | 1:2 | 218 | 100 |
| 5 | 1:4 | 152 | 100 |
| 6 | 1:8 | 868 | 100 |
| 7 | 1:16 | 2442 | 100 |
| 8 | 1:32 | 4166 | 100 |

DON
DataType: Median

| Location | Antibody Dose | DON | Total Events |
|---|---|---|---|
| 1 | 0 | 4 | 100 |
| 2 | 0 | 4 | 100 |
| 3 | Neat | 8 | 100 |
| 4 | 1:2 | 13 | 100 |
| 5 | 1:4 | 89 | 100 |
| 6 | 1:8 | 149 | 100 |
| 7 | 1:16 | 1451 | 100 |
| 8 | 1:32 | 2162 | 100 |

Protein Raw Data for Microsphere Binding for detection of Mycotoxins.
Program Luminex 100 IS
Build 2.2
Date Mar. 3, 2007 3:16:21 PM
SN LX10001089024
Session Operator 030307Afla.modbead.biotinAb
Samples 8 Min Events 0
Results
DataType: Median

| Location | Sample | Aflatoxin | Total Events |
|---|---|---|---|
| 1 | Blank | 10 | 100 |
| 2 | Blank | 10.5 | 100 |
| 3 | Neat Alfa | 105.5 | 100 |
| 4 | 1:02 | 217.5 | 100 |
| 5 | 1:02 | 152 | 100 |
| 6 | 1:02 | 868 | 100 |
| 7 | 1:02 | 2442 | 100 |
| 8 | 1:02 | 4165.5 | 100 |

DataType: Count

| Location | Sample | Aflatoxin | Total Events |
|---|---|---|---|
| 1 | Blank | 100 | 100 |
| 2 | Blank | 100 | 100 |
| 3 | Neat Alfa | 100 | 100 |
| 4 | 1:02 | 100 | 100 |
| 5 | 1:02 | 100 | 100 |
| 6 | 1:02 | 100 | 100 |
| 7 | 1:02 | 100 | 100 |
| 8 | 1:02 | 100 | 100 |

Program Luminex 100 IS
Build 2.2
Date Mar. 3, 2007 3:13:49 PM
SN LX10001089024
Session Operator 030307DONmodbead.antibiotin
Samples 8 Min Events 0
Results
DataType: Median

| Location | Sample | DON | Total Events |
|---|---|---|---|
| 1 | Blank | 3.5 | 100 |
| 2 | Blank | 3.5 | 100 |
| 3 | Neat Don | 7.5 | 100 |
| 4 | 1:02 | 12.5 | 100 |
| 5 | 1:02 | 89 | 100 |
| 6 | 1:02 | 148.5 | 100 |
| 7 | 1:02 | 1450.5 | 100 |
| 8 | 1:02 | 2161.5 | 100 |

DataType: Count

| Location | Sample | DON | Total Events |
|---|---|---|---|
| 1 | Blank | 100 | 100 |
| 2 | Blank | 100 | 100 |
| 3 | Neat Don | 100 | 100 |
| 4 | 1:02 | 100 | 100 |
| 5 | 1:02 | 100 | 100 |
| 6 | 1:02 | 100 | 100 |
| 7 | 1:02 | 100 | 100 |
| 8 | 1:02 | 100 | 100 |

The data indicate that mycotoxins or mycotoxin antigens can be bound to beads and can be used to detect in a competitive assay the presence of antibodies to mycotoxins in samples.

EXAMPLE 14

Detection of Fungal DNA and Mycotoxins in Animals

Findings for Dog (Necropsy, High Exposure to Environmental Molds):
 Liver and Lung:
 Mycotoxins: tricothecenes 0.96 ppb
 RT-PCR: *Penicillium chrysogenium* and *Aspergillus niger*
Findings for Horse (Urine):
 Tricothecenes: 5.32 ppb
Findings for Cat (Necropsy):
 Aflatoxin: 4 ppb

What is claimed is:

1. A method of quantifying a macrocyclic tricothecene mycotoxin in a patient tissue or a body fluid, the method comprising the steps of: extracting a recovering the tricothecene mycotoxin from the patient tissue or the body fluid wherein the body fluid is selected from the group consisting of a urine sample, a nasal secretion sample, a nasal wash sample, and sputum sample and wherein the patient has been exposed to mold; contacting the tricothecene mycotoxin with an antibody directed against the tricothecene mycotoxin to quantify the tricothecene mycotoxin, wherein the antibody detects macrocyclic tricothecenes; and quantifying the tricothecene mycotoxin to determine whether the patient has a fungal infection that produces macrocuclic tricothecenes wherein the sensitivity of the quantitation is 0.2 ng/ml.

2. The method of claim 1 wherein the tissue is derived from a patient tissue biopsy and is in a 10% formalin solution or is in a paraffin block.

3. A method of determining if a patient is at risk for or has developed a disease state related to a fungal infection that produces macrocyclic tricothecenes, the method comprising the steps of: extracting and recovering a macrocyclic tricothecene mycotoxin from a tissue or body fluid of the patient wherein the body fluid is selected from the group consisting of urine sample, a nasal secretion sample, a nasal wash sample, and a sputum sample wherein the patient has been exposed to mold; contacting the tricothecene mycotoxin with an antibody directed against the tricothecen mycotoxin, wherein the antibody detects macrocyclic tricothecenes; and quantifying the tricothecene mycotoxin to determine if the patient is at risk for or has developed the disease state related to the fungal infection that produces macrocyclic tricothecenes wherein the sensitivity of quantitation is 0.2 ng/ml.

4. The method of claim 3 further comprising the step of developing an effective treatment regimen for the patient.

5. The method of claim 3 wherein the tissue is derived from a patient tissue biopsy and is in a 10% formalin solution or is in a paraffin block.

6. The method of claim 1, wherein the tricothecene mycotoxin is contacted with the antibody using an enzyme-linked immunosorbent assay.

7. The method of claim 3 wherein the tricothecene mycotoxin is contacted with the antibody using an enzyme-linked immunosorbent assay.

8. The method of claim 1 further comprising the step of identifying the tricothecene mycotoxin using negative and positive control samples.

9. The method of claim 3, further comprising the step of identifying the tricothecene mycotoxin using negative and positive control samples.

10. The method of claim 1 further comprising the step of using calibration reagents to quantify the tricothecene mycotoxin.

11. The method of claim 3 further comprising the step of using calibration reagents to quantify the tricothecene mycotoxin.

12. The method of claim 1 wherein there is no detection of aflatoxins or ochratoxins.

13. The method of claim 3 wherein there is no detection of aflatoxins or ochratoxins.

* * * * *